US012698505B2

(12) United States Patent
Behr

(10) Patent No.: US 12,698,505 B2
(45) Date of Patent: Aug. 4, 2026

(54) EUKARYOTIC HOST SYSTEM FOR PRODUCING RECOMBINANT PROTEINS

(71) Applicant: Connor David Behr, Price, UT (US)

(72) Inventor: Connor David Behr, Price, UT (US)

(73) Assignee: Spero Technologies, Inc., Austin, TX (US)

( * ) Notice: Subject to any disclaimer, the term of this patent is extended or adjusted under 35 U.S.C. 154(b) by 1126 days.

(21) Appl. No.: 17/600,553

(22) PCT Filed: Mar. 31, 2020

(86) PCT No.: PCT/US2020/026010
§ 371 (c)(1),
(2) Date: Sep. 30, 2021

(87) PCT Pub. No.: WO2020/205890
PCT Pub. Date: Oct. 8, 2020

(65) Prior Publication Data
US 2022/0170031 A1 Jun. 2, 2022

Related U.S. Application Data

(60) Provisional application No. 62/827,685, filed on Apr. 1, 2019.

(51) Int. Cl.
*C12N 15/80* (2006.01)
*C12N 15/79* (2006.01)
*C12P 21/02* (2006.01)

(52) U.S. Cl.
CPC .............. *C12N 15/79* (2013.01); *C12P 21/02* (2013.01)

(58) Field of Classification Search
CPC .... C07K 14/4726; C07K 14/47; C07K 14/65; C12N 15/80; C12N 9/58; C12N 1/145; C12N 15/67; C12N 15/11; C12N 15/62; C12N 15/86; C12N 15/10; C12N 15/63; C12N 15/79; C12N 15/90
USPC ....................................................... 435/69.1
See application file for complete search history.

(56) References Cited

U.S. PATENT DOCUMENTS 3,854,278 A * 12/1974 Farr et al.

OTHER PUBLICATIONS

Burland et al. Gene 1993, 134(2) pp. 207-212.*
Minami et al. Minami', Biosci. Biotech. 2009, 73(3), pp. 747-749.*
Kwiatkowski et al., (Biochemistry 38:11643-11650, 1999.*
Kisselev L., (Structure, 2002, vol. 10: 8-9.*
Wristlock et al., (Quarterly Reviews of Biophysics 2003, vol. 36 (3): 307-340.*
Davos et al., (Proteins: Structure, Function and Genetics, 2000, vol. 41: 98-107.*
Brewer et al. Appld Microbiol., 1964, 12(2), pp. 161-164.*

* cited by examiner

*Primary Examiner* — Tekchand Saidha
*Assistant Examiner* — Mohammad Y Meah
(74) *Attorney, Agent, or Firm* — Lowenstein Sandler LLP

(57) ABSTRACT

Disclosed herein are eukaryotic host systems for producing recombinant proteins, eukaryotic hosts modified to produce recombinant proteins, and methods of producing recombinant proteins using the same. In certain embodiments, the eukaryotic host system is a plasmodium of the class Myxogastria, such as *Physarum polycephalum*, modified to produce one or more recombinant proteins, such as human insulin. In certain embodiments, a method of protein production includes collecting one or more recombinant proteins produced by *Physarum polycephalum* while in a form of multinucleate plasmodia.

14 Claims, 5 Drawing Sheets

Specification includes a Sequence Listing.

GROWTH CHAMBER
200

GROWTH CHAMBER
200

EUKARYOTIC HOST SYSTEM FOR PRODUCING RECOMBINANT PROTEINS

CROSS-REFERENCE TO RELATED APPLICATIONS APPLICATION

This application is a national stage entry under 35 U.S.C. § 371 of International Application No. PCT/US2020/026010, filed on Mar. 31, 2020, which claims the benefit of priority of U.S. Provisional Patent Application No. 62/827,685, filed on Apr. 1, 2019, the disclosures of which are hereby incorporated by reference herein in their entireties.

REFERENCE TO SEQUENCE LISTING SUBMITTED ELECTRONICALLY VIA EFS-WEB

The content of the electronically submitted Sequence Listing (file name: 33412_25_SL.txt; date of creation: Feb. 13, 2020; file size: 25,226 bytes) is hereby incorporated by reference herein in its entirety.

TECHNICAL FIELD

The present disclosure directed to protein production and, more specifically, to the production of recombinant proteins using eukaryotic hosts and expression systems.

BACKGROUND

Methods for producing proteins are of great importance to medicine and medical research, and include bacterial-based production systems, yeast-based production systems, and chemically-based systems. In the case of production in bacteria and yeast, the cells are modified with recombinant DNA and grown in fermentation tanks, after which the target protein is extracted and purified.

Recombinant insulin is of particular interest as its demand has continued to increase with the significant global growth in the number of individuals diagnosed with diabetes. Such demand has put pressure on current insulin production technologies to reduce costs and improve yields of biologically functional insulin. It is desirable that future systems maintain high throughput while also providing mechanisms for efficiently performing posttranslational modifications and facilitating protein folding.

SUMMARY

The following summary presents a simplified summary of various aspects of the present disclosure in order to provide a basic understanding of such aspects. This summary is not an extensive overview of the disclosure. It is intended to neither identify key or critical elements of the disclosure, nor delineate any scope of the particular embodiments of the disclosure or any scope of the claims. Its purpose is to present some concepts of the disclosure in a simplified form as a prelude to the more detailed description that is presented later.

Aspects of the present disclosure relate to eukaryotic host systems (e.g., modified *Physarum polycephalum*) for producing recombinant proteins (e.g., therapeutic proteins).

In one aspect of the present disclosure, a method of protein production comprises collecting one or more recombinant proteins produced (e.g., secreted) by *Physarum polycephalum* while in a form of multinucleate plasmodia. The *Physarum polycephalum* comprises a nucleic acid sequence that, when expressed by the *Physarum polycephalum*, results in the production of the one or more recombinant proteins. In one embodiment, the method comprises: transforming the *Physarum polycephalum* with the nucleic acid sequence while the *Physarum polycephalum* are in an amoeboid phase; and culturing the transformed *Physarum polycephalum* under conditions that promote formation of the multinucleate plasmodia.

In one embodiment, the multinucleate plasmodia are macroplasmodia. In one embodiment, the method further comprises: growing the *Physarum polycephalum* under conditions suitable to promote a transition of the *Physarum polycephalum* from the amoeboid phase into microplasmodia; transferring the microplasmodia to a growth chamber; and culturing the microplasmodia under conditions that promote formation of macroplasmodia on one or more interior surfaces of the growth chamber. In one embodiment, the method further comprises transforming the *Physarum polycephalum* with the nucleic acid sequence while the *Physarum polycephalum* are in the form of the multinucleate plasmodia. In one embodiment, the method further comprises transforming the *Physarum polycephalum* with the nucleic acid sequence, wherein the nucleic acid sequence is chromosomally-integrated into the *Physarum polycephalum*.

In one embodiment, collecting the one or more recombinant proteins comprises: adding a buffer solution to a growth chamber containing the *Physarum polycephalum*; and removing at least a portion of the buffer solution from the growth chamber. In one embodiment, the method further comprises separating the one or more recombinant proteins from other components within the buffer solution.

In one embodiment, the *Physarum polycephalum* is diploid when in the form of the multinucleate plasmodia.

In one embodiment, the one or more recombinant proteins comprise human insulin or a functional variant thereof. In one embodiment, the one or more recombinant proteins comprise human insulin and one or more of proprotein convertase 1 (PC1), proprotein convertase 2 (PC2), carboxypeptidase E (CPE), neuroendocrine protein 7B2, furin, functional variants thereof, or combinations thereof. In one embodiment, the one or more recombinant proteins comprise human insulin, PC1, PC2, and CPE, or functional variants thereof.

In another aspect of the present disclosure, a method of protein production comprises collecting human insulin, or a functional variant thereof, produced by *Physarum polycephalum*, the *Physarum polycephalum* comprising a nucleic acid sequence that, when expressed by the *Physarum polycephalum*, results in the production of the human insulin or the functional variant thereof. In one embodiment, the *Physarum polycephalum* is in a form of multinucleate plasmodia. In one embodiment, the method further comprises: transforming the *Physarum polycephalum* with the nucleic acid sequence while the *Physarum polycephalum* are in an amoeboid phase; and culturing the transformed *Physarum polycephalum* under conditions that promote formation of the multinucleate plasmodia.

In one embodiment, the multinucleate plasmodia are macroplasmodia. In one embodiment, the method further comprises: growing the *Physarum polycephalum* under conditions suitable to promote a transition of the *Physarum polycephalum* from the amoeboid phase into microplasmodia; transferring the microplasmodia to a growth chamber; and culturing the microplasmodia under conditions that promote formation of macroplasmodia on one or more interior surfaces of the growth chamber. In one embodiment, the method further comprises transforming the *Physarum polycephalum* with the nucleic acid sequence while the *Physarum polycephalum* are in the form of multinucleate plasmodia. In one embodiment, the method further comprises transforming the *Physarum polycephalum* with the nucleic acid sequence, wherein the nucleic acid sequence is chromosomally-integrated into the *Physarum polycephalum*.

In one embodiment, collecting the human insulin comprises: adding a buffer solution to a growth chamber containing the *Physarum polycephalum*; and removing at least a portion of the buffer solution from the growth chamber. In one embodiment, the method further comprises separating the human insulin from other components within the buffer solution.

In one embodiment, the *Physarum polycephalum* is diploid when in the form of the multinucleate plasmodia.

In one embodiment, the nucleic acid sequence encodes for preproinsulin, PC1, PC2, CPE, neuroendocrine protein 7B2, furin, functional variants thereof, or combinations thereof. In one embodiment, the nucleic acid sequence further encodes for preproinsulin, PC1, PC2, and CPE, or functional variants thereof.

In another aspect of the present disclosure, a system for protein production comprises: a growth chamber; and multinucleate plasmodia of *Physarum polycephalum* disposed within the growth chamber, wherein the *Physarum polycephalum* comprise a nucleic acid sequence that, when expressed by the *Physarum polycephalum*, results in the production of one or more recombinant proteins. In one embodiment, one or more recombinant proteins comprise human insulin or a functional variant thereof. In one embodiment, the one or more recombinant proteins comprise human insulin and one or more of PC1, PC2, CPE, neuroendocrine protein 7B2, furin, functional variants thereof, or combinations thereof. In one embodiment, the one or more recombinant proteins comprise human insulin, PC1, PC2, CPE, or functional variants thereof.

In one embodiment, the system may be used to perform any of the aforementioned methods.

Another aspect of the present disclosure is directed to *Physarum polycephalum* modified to produce human insulin or a functional variant thereof.

Another aspect of the present disclosure is directed to *Physarum polycephalum* modified to produce human insulin.

Another aspect of the present disclosure is directed to *Physarum polycephalum* modified to produce human insulin, PC1, PC2, CPE, neuroendocrine protein 7B2, furin, functional variants thereof, or combinations thereof.

Another aspect of the present disclosure is directed to *Physarum polycephalum* modified to produce human insulin, PC1, PC2, and CPE, or functional variants thereof.

Another aspect of the present disclosure is directed to *Physarum polycephalum* modified to produce human insulin, PC1, PC2, and CPE.

Another aspect of the present disclosure is directed to a multinucleate *plasmodium* of the class Myxogastria modified to produce human insulin or a functional variant thereof.

Another aspect of the present disclosure is directed to a multinucleate *plasmodium* of the class Myxogastria modified to produce human insulin.

Another aspect of the present disclosure is directed to a multinucleate *plasmodium* of the class Myxogastria modified to produce human insulin, PC1, PC2, CPE, neuroendocrine protein 7B2, furin, functional variants thereof, or combinations thereof.

Another aspect of the present disclosure is directed to a multinucleate *plasmodium* of the class Myxogastria modified to produce human insulin, PC1, PC2, and CPE, or functional variants thereof.

Another aspect of the present disclosure is directed to a multinucleate *plasmodium* of the class Myxogastria modified to produce human insulin, PC1, PC2, and CPE.

In another aspect of the present disclosure, a system for protein production comprises: a growth chamber; and multinucleate plasmodia of the class Myxogastria disposed within the growth chamber, wherein the multinucleate plasmodia comprise a nucleic acid sequence encoding for one or more recombinant proteins.

In certain embodiments, the aforementioned nucleic acid sequences may further encode any of the aforementioned proteins to be expressed with a secretion tag. In certain embodiments, the secretion tag is a non-native secretion tag (i.e., not naturally produced by *Physarum polycephalum*). In certain embodiments, the secretion tag is native to the class Dictyostelia. In certain embodiments, the secretion tag is native to *Dictyostehum discoideum*. In certain embodiments, a nucleic acid sequence encodes for preproinsulin tagged with a secretion tag, such as a secretion tag that is native to *Dictyostehum discoideum*.

In certain embodiments, the aforementioned nucleic acid sequences may further encode one or more 2A self-cleaving peptides. In certain embodiments, a nucleic acid sequence encoding one or more recombinant proteins may further encode one or more 2A self-cleaving peptides between each encoded recombinant protein and its upstream or downstream neighboring recombinant protein sequence. In certain embodiments, the 2A self-cleaving peptides comprise P2A or E2A.

As used herein, the singular forms "a," "an," and "the" include plural references unless the context clearly indicates otherwise. Thus, for example, reference to "a protein" can include a single protein, multiple proteins of a single type, and mixtures of two or more different proteins.

Also as used herein, the term "about" in connection with a measured quantity, refers to the normal variations in that measured quantity, as expected by one of ordinary skill in the art in making the measurement and exercising a level of care commensurate with the objective of measurement and the precision of the measuring equipment. In certain embodiments, the term "about" includes the recited number ±1%, such that "about 10" would include 9.9 to 10.1 and all values in between.

Also as used herein, "protein" has its ordinary and customary meaning in the art and includes, and refers to a polypeptide (i.e., a string of at least two amino acids linked to one another by peptide bonds). Polypeptides may include natural amino acids, non-natural amino acids, synthetic amino acids, amino acid analogs, and combinations thereof. The term "peptide" is typically used to refer to a polypeptide having a length of less than about 50 amino acids. Proteins may include moieties other than amino acids (e.g., glycoproteins) and may be processed or modified. A protein can be a complete polypeptide chain as produced by a cell, or can be a functional portion thereof. A protein can include more than one polypeptide chain which may be chemically linked (e.g., by a disulfide bond), non-chemically linked (e.g., by hydrogen bonding), or both. Polypeptides may contain L-amino acids, D-amino acids, or both, and may contain any of a variety of amino acid modifications or analogs known in the art.

Also as used herein, "nucleic acid," "polynucleic acid," and "nucleic acid sequence" have their ordinary and customary meaning in the art and include any polymeric nucleic acid such as DNA or RNA molecules, as well as chemical derivatives known to those skilled in the art (e.g., peptide nucleic acids). Nucleic acid sequences include not only those encoding a protein, but also include sequences that can be used to decrease the expression of a targeted nucleic acid sequence using techniques known in the art (e.g., antisense, interfering, or small interfering nucleic acids). Nucleic acid sequences can also be used to initiate or increase the expression of a targeted nucleic acid sequence or the production of a targeted protein within a host cell. The terms "nucleic acid," "polynucleic acid," and "nucleic acid sequence" may be used interchangeably, and may be in single-stranded or double-stranded form unless the context requires or suggests a particular form.

Also as used herein, "exogenous" nucleic acids or genes are those that do not occur in nature in the vector utilized for nucleic acid transfer. The term is not intended to exclude nucleic acids encoding a protein or polypeptide that occurs naturally in the patient or host.

Also as used herein, "host organism," "host system," "host cell," and "host" refer generally to any organism that has been genetically modified to express a gene in whole or in part that does not naturally occur in that organism or cell.

Also as used herein, "functional variant" refers to a variant of the protein that is capable of, partially or completely, fulfilling the function of the naturally occurring corresponding protein. Functional variants of a protein may include, for example, proteins which differ from their naturally occurring counterparts by one or more amino acid substitutions, deletions or additions.

BRIEF DESCRIPTION OF THE DRAWINGS

The present disclosure is illustrated by way of example, and not by way of limitation, in the figures of the accompanying drawings, in which.

DETAILED DESCRIPTION

Figure 1:
FIG. 1 is a generalized flow chart of a method for producing recombinant proteins in accordance with certain embodiments.
Figure 1:
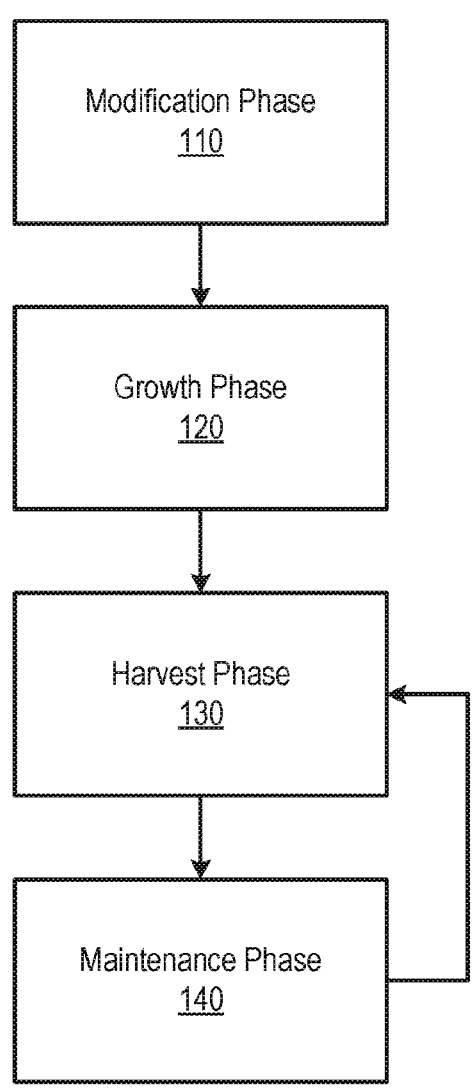

The present invention is directed to eukaryotic host systems for producing recombinant proteins, eukaryotic hosts modified to express recombinant proteins, and methods of producing recombinant proteins using the same. In a non-limiting example, the eukaryotic host system is a plasmodium of the class Myxogastria, such as *Physarum polycephalum*, modified to produce (i.e., express) one or more therapeutic proteins. In another non-limiting example, the recombinant proteins include therapeutic proteins. In another non-limiting example, a therapeutic protein includes human insulin.

Human insulin is naturally produced in the pancreas by beta cells. These cells first transcribe the insulin gene into RNA, which exits the nucleus and is processed by the endoplasmic reticulum where it is translated into a protein called preproinsulin. Preproinsulin is not biologically functional at this stage, and is further folded inside the endoplasmic reticulum where a portion of the beginning amino acid sequence is trimmed to produce proinsulin. At this stage, the proinsulin includes an A chain and a B chain, which are folded over each other and bound together. The proinsulin then reaches the golgi apparatus where it is loaded into secretory vesicles. The cell simultaneously produces PC1, PC2, and CPE proteins, which follow a similar processing route as insulin and are ultimately loaded into the secretory vesicles with the proinsulin.

While under acidic conditions in the secretory vesicles, the PC1, PC2, and CPE proteins cut and trim the proinsulin into three different pieces: the A chain, the B chain, and a C-peptide. This results in a functional insulin having an A chain and B chain linked together in the middle and cut at the ends. When the beta cells detect high blood glucose levels, the secretory vesicles containing insulin, C-peptide, PC1, PC2, and CPE are released into the blood.

"Synthetic human insulin" refers to any human insulin that is synthetically produced (i.e., produced outside of the human body through chemical means or by a host organism adapted to express human insulin), and may be chemically and structurally identical to naturally-produced human insulin. An illustrative synthetic process utilizing a host organism is now described. First, nucleic acid sequences encoding for the A chain and the B chain of insulin are inserted into an organism. The nucleic acid sequences encoding for the A chain and the B chain are separately inserted in bacteria. In yeast, however, the nucleic acid sequences encoding the A chain and the B chain are inserted as a single modified sequence (i.e., the natural sequence with a new signal peptide and linking peptide in the place of C-peptide). The bacteria or yeast are then placed into one or more large metal bioreactors containing growth media. The bioreactors are regulated by a control system to maintain optimal temperature, oxygenation, and mechanical agitation for promoting growth.

In bacteria, the A chains and B chains are produced separately. Because bacteria lack endoplasmic reticuli, the two chains remain unbound and the formation of disulfide bridges between the two chains must be performed in a separate reaction. Once the bacteria have grown to their limit in the bioreactor, the bioreactor is drained and the organisms are lysed, releasing the A chains and B chains in the lysate (this requires consecutive batches of the bacteria to be regrown). The A chains and B chains are purified out of the lysate then chemically treated to bind them together in the middle. In yeast, which do possess endoplasmic reticuli, the A chain, B chain, and C-peptide are produced, and the A and B chains are bound by disulfide bridges. However, yeast cells lack the enzymes required to cut out the linking peptide, which requires obtaining the intermediate product from the yeast and performing a further reaction. Regardless of the organism used, the completed insulin is purified once again, quality tested, and packaged for distribution and use.

Certain embodiments of the present disclosure utilize *Physarum polycephalum* as a host system for producing therapeutic recombinant proteins, such as human insulin. *Physarum polycephalum* is a fungus-like eukaryotic organism of the order Physarales of the class Myxogastria, a class of organisms commonly referred to as "slime molds." The life cycles of *Physarum polycephalum* and other related organisms are characterized by a distinctive multinucleate trophic stage referred to as a "plasmodium." *Physarum polycephalum* is typically found in its plasmodial form on decaying plant material. *Physarum polycephalum* has been the subject of much research due to its rapid growth rate, ease of culturing, and its ability to adapt to changing environmental conditions. However, there have been no studies characterizing its potential as a protein production platform, and particularly for producing therapeutic recombinant proteins such as human insulin.

Certain embodiments of the present disclosure utilize *Physarum polycephalum* to produce human insulin in a process similar to how human insulin is produced naturally. The embodiments leverage several characteristics of *Physarum polycephalum* that include the following: (1) it is a multinucleated organism with a single cell being capable of housing millions of nuclei; (2) it is biologically immortal and can continue to grow exponentially within the constraints imposed by physical space and access to food and water; (3) it is a eukaryotic organism that utilizes endoplasmic reticuli in its protein expression pathway; and (4) it is able to grow rapidly due in part to its relatively large amount of nuclei, ribosomes, and other cellular machinery.

In certain embodiments, *Physarum polycephalum* is modified with a nucleic acid sequence encoding human preproinsulin along with, for example, PC1, PC2, and CPE to process the preproinsulin into a protein that is chemically-equivalent or substantially-chemically equivalent to human insulin. When in its plasmodial form, the numerous nuclei of a single modified *Physarum polycephalum* cell can mass produce preproinsulin RNA molecules. The RNA molecules are then translated by ribosomes into preproinsulin proteins, which are then processed by the cell's numerous endoplasmic reticuli to form proinsulin proteins. The proinsulin proteins are then transported to the golgi apparati where they are packaged into secretory vesicles along with PC1, PC2, and CPE. The proinsulin proteins are processed into mature insulin proteins and then secreted as functional human insulin, C-peptide, PC1, PC2, CPE, and other proteins.

In some embodiments, proteins produced by *Physarum polycephalum* may be collected after secretion (e.g., adding a buffer solution to a chamber housing the *Physarum polycephalum* and collecting the buffer solution containing the proteins). In other embodiments, *Physarum polycephalum* may be lysed and the proteins may be purified from the lysate.

These embodiments and others described in the present disclosure have several advantages over traditional methods of protein production. The embodiments advantageously reduce time, energy, cost, and materials required to produce therapeutic proteins (such as human insulin) compared to other synthetic methods of producing therapeutic protein. The embodiments further advantageously allow for protein production in a manner that mimics natural protein production in the human body without requiring additional chemical processing or purification steps to identify properly formed or functional proteins. The embodiments further advantageously allow for continuous production of proteins from a single batch of *Physarum polycephalum* without the need to regenerate or grow a new batch after each collection step; modified *Physarum polycephalum* can be grown under non-stringent conditions, and harvesting of the proteins can be performed simply by rinsing secreted proteins with a buffer solution and collecting the buffer. The embodiments further advantageously allow for human insulin and other proteins to be produced concurrently, which may also assist in the treatment of diabetes. Moreover, multiple proteins, including combinations of proteins from different organisms, may be produced concurrently together. It is contemplated that the embodiments described herein may be adapted to produce other types of molecules using *Physarum polycephalum*, including chemicals for foods, reagents, medications, fuels, and other molecules, which may have applications in research, medicine, stem cell research, food production, and energy production.

In some embodiments, a system for protein production may include a growth chamber for growing and maintaining *Physarum polycephalum* as a multinucleate plasmodium. It is contemplated that such systems may be used to advantageously produce therapeutic proteins, such as human insulin, on a large scale. It is further contemplated that such embodiments overcome problems with oxygenation in current reactor systems, which often require high pressure oxygen gas flow injections into large reactor volumes to maintain adequate oxygenation. *Physarum polycephalum* may be cultured in air, eliminating the need for precise control of temperature, pH, oxygenation, stirring, and several other costly processes.

It is further contemplated that the embodiments described herein have utility in point-of-care therapeutics, which would allow medical professionals and patients themselves to produce medications directly in a hospital setting or at home using only a single device and relatively few inexpensive standard mixtures. Because such devices could be made larger for higher production and the mixtures can be powdered for long term storage and transportation, such systems could also be used in disaster relief to produce much needed medications, antibiotics, and potentially even diagnostic reagents. The embodiments described herein may facilitate distribution of medical resources to impoverished and developing areas, both domestic and abroad.

It is further contemplated that smaller-scale systems may be used outside of a clinical or manufacturing setting to advantageously produce therapeutic proteins needed to treat an individual or community of individuals. For example, small-scale systems based on the embodiments described herein may allow for individuals to maintain their own insulin production systems by growing and maintaining *Physarum polycephalum* that has been modified to produce human insulin, and easily purifying the resulting human insulin from the reaction chamber containing the *Physarum polycephalum*. Such systems would be relatively inexpensive in comparison to the current market price of insulin, and would allow for the production of sufficient quantities of insulin for communities that lack resources and medical infrastructure.

In some embodiments, a eukaryotic host cell (e.g., *Physarum polycephalum*) is modified by introducing a gene encoding for one or more target proteins (e.g., therapeutic proteins), functional variants thereof, fragments thereof, and/or precursors thereof. The embodiments may utilize both non-viral expression constructs (vectors) or viral vectors. The vector can be an episomal vector, i.e., one that is capable of self-replicating autonomously within the host cell, or an integrating vector, i.e., one which stably incorporates into the genome of the cell. The expression in the host cell can be constitutive or regulated (e.g. inducible).

Non-viral vectors permit the in vivo expression of protein in the host cells, and may be in a form of, for example, a plasmid, a modified RNA, a cDNA, antisense oligomers, DNA-lipid complexes, nanoparticles, exosomes, any other suitable non-viral shuttle known to those of ordinary skill in the art, variations thereof, and combinations thereof. Suitable methods for the transfer of non-viral vectors into host cells include, for example, the lipofection method, the calcium-phosphate co-precipitation method, the diethylami-noethyl-dextran method, and direct DNA introduction methods using micro-glass tubes, ultrasound, electroporation, chemical poration, sonoporation, magnetofection, particle bombardment, and the like. Prior to the introduction of the vector, the host cells may be treated with a permeabilization agent, such as phosphatidylcholine, streptolysins, sodium caprate, decanoylcarnitine, tartaric acid, lysolecithin, Triton X-100, and the like.

In some embodiments, a viral vector is used. Viral vectors may comprise a viral genome in which a portion of the native sequence has been deleted in order to introduce a heterogeneous nucleic acid sequence without destroying the infectivity of the virus. Due to the specific interaction between virus components and host cell receptors, viral vectors are highly suitable for efficient transfer of genes into target cells. Suitable viral vectors for facilitating gene transfer into a host cell can be derived from different types of viruses.

Other vector delivery systems which can be employed to deliver a nucleic acid sequence into host cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific. Receptor-mediated gene targeting vehicles may include two components: a cell receptor-specific ligand and a DNA-binding agent.

In some embodiments, nuclease systems may also be used, in conjunction with a vector and/or an electroporation system, to introduce a nucleic acid sequence into host cells. Exemplary nuclease systems may include, without limitations, clustered regularly interspaced short palindromic repeats (CRISPR), a DNA cutting enzyme (e.g., Cas9), meganucleases, transcription activator-like effector nucleases (TALENs), zinc finger nucleases, any other suitable nuclease system, variations thereof, and combinations thereof. For example, in one embodiment, one vector may be used for a nuclease (e.g., CRISPR) and another vector may be used for a DNA cutting enzyme (e.g., Cas9) to introduce both the nuclease and the DNA cutting enzyme into a host cell.

In some embodiments, the vector may comprise a promoter that is functionally linked to the nucleic acid sequence encoding the target proteins, functional variants thereof, fragments thereof, and/or precursors thereof. In some embodiments, the vector comprises a promoter specific to the host cell that may result in an activity which is at least 5-fold, at least 10-fold, at least 15-fold, at least 20-fold, at least 25-fold, or at least 50-fold higher compared to its activity in a different type of cell.

The vectors useful in the embodiments described herein may have varying transduction efficiencies. More than one vector (viral or non-viral, or combinations thereof) can be used simultaneously, or in sequence. This can be used to transfer more than one polynucleotide, and/or target more than one type of cell. Where multiple vectors or multiple agents are used, more than one transduction/transfection efficiency can result.

The proteins produced by the embodiments described herein may also be functional variants of target proteins, and may exhibit a significant amino acid sequence identity compared to the target protein. For instance, the amino acid identity may amount to at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99%.

The amino acid substitutions can be conservative or non-conservative. It is preferred that the substitutions are conservative substitutions, i.e., a substitution of an amino acid residue by an amino acid of similar polarity, which acts as a functional equivalent. Preferably, the amino acid residue used as a substitute is selected from the same group of amino acids as the amino acid residue to be substituted. For example, a hydrophobic residue can be substituted with another hydrophobic residue, or a polar residue can be substituted with another polar residue having the same charge. Functionally homologous amino acids that may be used for a conservative substitution may comprise, for example, non-polar amino acids such as glycine, valine, alanine, isoleucine, leucine, methionine, proline, phenylalanine, and tryptophan. Examples of uncharged polar amino acids may comprise serine, threonine, glutamine, asparagine, tyrosine, and cysteine. Examples of charged polar (basic) amino acids comprise histidine, arginine, and lysine. Examples of charged polar (acidic) amino acids comprise aspartic acid and glutamic acid.

Also considered as functional variants are proteins which differ from their naturally occurring counterparts by one or more (e.g., 2, 3, 4, 5, 10, 15, etc.) additional amino acids. These additional amino acids may be present within the amino acid sequence of the original protein (i.e., as an insertion), or they may be added to one or both termini of the protein. Basically, insertions can take place at any position if the addition of amino acids does not impair the capability of the polypeptide to fulfill the function of the naturally occurring protein. Moreover, variants of proteins also comprise proteins in which, compared to the original polypeptide, one or more amino acids are lacking. Such deletions may affect any amino acid position provided that it does not impair the ability to fulfill the normal function of the protein.

Finally, functional variants of proteins also refer to proteins which differ from the naturally occurring protein by structural modifications, such as modified amino acids. Modified amino acids are amino acids which have been modified either by natural processes, such as processing or post-translational modifications, or by chemical modification processes known in the art. Typical amino acid modifications comprise phosphorylation, glycosylation, acety-lation, O-linked N-acetylglucosamination, glutathionylation, acylation, branching, ADP ribosylation, crosslinking, disulfide bridge formation, formylation, hydroxylation, carboxylation, methylation, demethylation, amidation, cyclization and/or covalent or non-covalent bonding to phosphotidylinositol, flavine derivatives, lipoteichonic acids, fatty acids, or lipids.

In some embodiments of the present invention, the method is able to produce a variety of organic compounds, including biologics or biofuels. Biologics are generally considered to be large, complex molecules which are often produced by living cells and organisms naturally or through genetic engineering. Biologics may be used for a variety of uses, including disease treatments, diagnostics and prevention of a variety of health conditions. In some embodiments, the biologics may be allergenics, antibodies, blood products or derivatives thereof, enzymes, growth factors, hormones, immunomodulators, interferons, interleukins, polypeptides, proteins, serums, tissues, toxins, and vaccines.

In other embodiments, where the biologic is a hormone, the hormone may be, but is not limited to, adiponectin, adrenocorticotropic hormone, androgen, angiotensinogen, antidiuretic hormone, amylin, atrial-natriuretic peptide, brain natriuretic peptide, cacitonin, cholecystokinin, cortisol, corticotrophin-releasing hormone, cortistatin, enkephalin, endothelin, epinephrine, estrogen, erythropoietin, follicle-stimulating hormone, galanin, gastric inhibitory polypeptide, gastrin, ghrelin, glucagon, glucagon-like peptide-1, glucocorticoid, gonadotropin-releasing hormone, growth hormone, growth hormone-releasing hormone, hepcidin, human chorionic gonadotropin, human placental lactogen, humoral factors, inhibin, insulin (e.g., human insulin), insulin-like growth factor, leptin, leukotriene, lipotropin, luteinizing hormone, melatonin, melanocyte stimulating hormone, mineralocorticoid, motilin, orexin, oxytocin, pancreatic polypeptide, parathyroid, pituitary adenlate cyclase-activating peptide, progesterone, prolactin, prolactin releasing hormone, prostacyclin, prostaglandins, relaxin, renin, secosteroid, secretin, somatostatin, testosterone, thrombopoietin, thromboxane, thyroid-stimulating hormone, thyrotropin-releasing hormone, thyroxine, triiodothyronine, vasoactive intestinal peptide, or combinations thereof.

In addition, some embodiments of the present invention may be used to produce proteins for treating conditions including, but not limited to, ankylosing spondylitis, autoimmune diseases, various cancers, Crohn's disease, diabetes, gout, indeterminate colitis, inflammatory bowel disease, psoriasis, psoriatic arthritis, rheumatoid arthritis, ulcerative colitis, uveitis, and viral infection.

The methods described herein are contemplated for producing other types of biomolecules, including, but not limited to, spider silk, cartilage, exoskeleton structures, and the like. The methods are further contemplated for the production of biofuels, such as ethanol. Biofuels are considered to be energy sources derived from organic materials. Biofuels are most widely used in liquid form which may be more easily integrated into currently used systems. Biofuels also have the feature of being transportable sources of energy. The use of biofuels may be preferable to other renewable energy sources, such as wind, solar, hydrothermal, and tidal flows, which would require additional input to make these other energy sources compatible with presently used infrastructure. Biofuels may be produced through fermentation of organic material or through extraction of lipids, vegetable oils, and animal fats. To increase the efficiency of production of ethanol, for example, some embodiments of the present invention allow for genetically engineered organisms (e.g., modified *Physarum polycephalum*) to produce biofuels directly or enzymes for use in producing biofuels. In some embodiments, where the organic compound is a biofuel, the biofuel may be, but is not limited, biodiesel, biogas, butanol, ethanol, or methanol.

In some embodiments, host cells may be modified to include a selectable marker. To ensure a gene is properly integrated into the genome of the host organism or cell, a selectable marker may be used. A selectable marker is generally a gene or part of a gene which is also inserted with a gene of interest. The selectable marker provides an additional, non-native characteristic to the organism to distinguish the organisms with the gene of interest and selectable marker from the organisms without it. In some embodiments, the selectable marker may be a drug resistance marker, a multidrug resistance marker, a metabolic survival marker, a color marker, a fluorescent marker, or a combination thereof. In particular embodiments, the selectable marker may be a dihydrofolate reductase gene, a guanosine phosphoribosyl transferase (GPT) gene, a histidinol resistance gene, a hygromycin resistance gene, a β-galactosidase gene, a green fluorescent protein gene, a red fluorescent protein gene, a blue fluorescent protein gene, a yellow fluorescent protein gene, a DsRed fluorescent protein gene, a zeomycin resistance gene, a zeocin resistance gene, a puromycin resistance gene, a blacsticidin S resistance gene, a spectinomycin resistance gene, a streptomycin resistance gene, a neomycin resistance gene, or a combination thereof. In embodiments utilizing *Physarum polycephalum*, which may be in its multinucleate plasmodial form, selectable markers may be used to identify which nuclei of the host cell the gene has been integrated into.

The production of various cellular products, including but not limited to, fatty acids, amino acids, and ethanol, or the production of enzymes used to facilitate the production of such cellular products, are contemplated in some embodiments. Fatty acid synthesis occurs through the Type-I and Type-II fatty acid synthases and is encoded by the FASN gene and its homologs thereof. In some embodiments, a host cell may be modified to include the FAS1, FAS2, FASN genes, homologs, or combinations thereof. The addition of the FAS1, FAS2, FASN genes, homologs, or combinations thereof may help to increase fatty acid synthesis in some embodiments. Similarly, an increase in fatty acid production may increase the amount of animal fat in modified organisms, which may increase the amount of biofuel and biodiesel produced.

Amino acids are essential for protein synthesis, and the production of amino acids varies greatly depending on the organism. In some organisms, particular amino acids cannot be synthesized by the organism, as is the case with humans. In some embodiments, host cells may be further modified to include a gene for an amino acid producing enzyme. In some embodiments, the amino acid producing enzyme may be for the production of an amino acid including, but not limited, alanine, arginine, aspartate, asparagine, cysteine, glutamate, glutamine, glycine, histidine, isoleucine, leucine, lysine, methionine, phenylalanine, proline, serine, threonine, tyrosine, tryptophan, or valine.

FIG. 1 illustrates a method 100 of producing proteins (e.g., therapeutic recombinant proteins) in accordance with certain embodiments. The method 100 discusses the use of *Physarum polycephalum* as a host organism, but it is to be understood that the method may be adapted to utilize other organisms similar to *Physarum polycephalum* (e.g., organisms of the class Myxogastria that may have similar characteristics as *Physarum polycephalum*).

The method 100 begins at a modification phase 110 where *Physarum polycephalum* cells are modified with a nucleic acid sequence that, when expressed by the *Physarum polycephalum*, results in the production of target proteins. The nucleic acid sequence may encode for specific target proteins, precursors to the target proteins, and/or other proteins that may facilitate formation and/or modification of the target proteins. In some embodiments, the *Physarum polycephalum* cells are transformed with the nucleic acid sequence while still in their amoeboid phase (i.e., each cell contains a single nucleus). The amoeboid cells may be haploid amoebae, diploid amoebae, or a combination thereof. In some embodiments, the *Physarum polycephalum* cells are transformed with the nucleic acid sequence while in the form of multinucleate plasmodia. In some embodiments, transformation results in chromosomal-integration of the nucleic acid sequence into the *Physarum polycephalum* cells (i.e., into the nuclei thereof).

The method 100 then proceeds to a growth phase 120. During the growth phase 120, the *Physarum polycephalum* cells are grown under conditions suitable to promote a transition from the amoeboid phase into a microplasmodial phase. The microplasmodia may then be transferred to a growth chamber where they are cultured in a growth media. The conditions of the growth chamber promote fusion of the cells until they form multinucleate plasmodia of a target size. In some embodiments, multiple growth chambers may be utilized to maintain macroplasmodia in a one-to-one fashion (e.g., one chamber per macroplasmodium).

Once the multinucleate plasmodia reach the target size, the method 100 then proceeds to a harvest phase 130. During the harvest phase 130, target proteins that have been secreted by the *Physarum polycephalum* macroplasmodia may be collected, for example, by rinsing with a buffer solution and collecting the buffer solution. The proteins may be purified from the collected buffer solution and used in downstream applications. In some embodiments, at least some of the *Physarum polycephalum* macroplasmodia are lysed, and their lysates may be collected and purified to obtain the target proteins.

The method 100 then proceeds to a maintenance phase 140. During the maintenance phase 140, the *Physarum polycephalum* macroplasmodia are maintained by providing additional food and water, and cleaning the reaction chamber in which they are housed. If the macroplasmodia reach a size that exceeds the growth chamber capacity or is close to exceeding the growth chamber capacity, the macroplasmodia may be pruned to maintain a desired size. Target proteins may continue to be collected during the maintenance phase. The harvest phase 130 may be repeated, followed by the maintenance phase 140 in a cyclic fashion until a desired amount of target protein is produced and collected. In some embodiments, an antibiotic may be added to the growth chamber to maintain sterility, and the *Physarum polycephalum* may be modified to exhibit resistance to the antibiotic (e.g., hygromycin B may be used, and the *Physarum polycephalum* is modified to be hygromycin resistant).

While FIG. 1 illustrates a flow chart demonstrating the exemplary method 100, it should be understood that modifications to the method 100 are within the scope of this disclosure. The ordering of the phases may be performed differently than as described, as would be appreciated by one of ordinary skill in the art. Some of the phases may be omitted or repeated, and other phases may be added. Moreover, the method 100 may be fully automated in some embodiments.

Figure 2A:
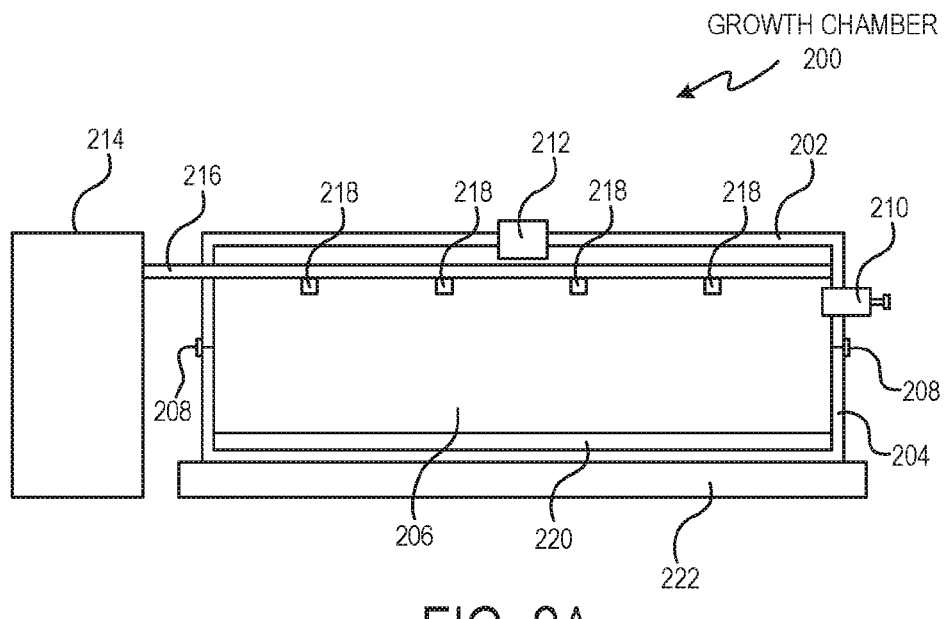
FIG. 2A is a schematic illustrating a side cross-sectional view of an exemplary growth chamber for use in accordance with certain embodiments.
Figure 2B:
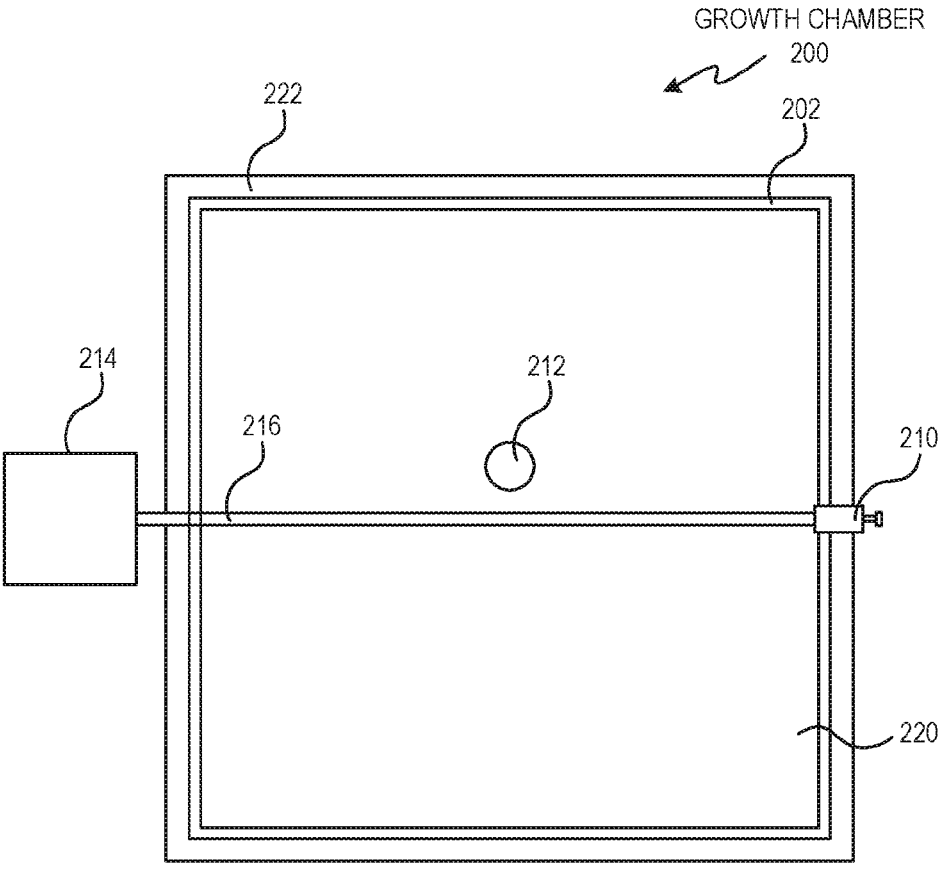
FIG. 2B is a schematic illustrating a top view of the exemplary growth chamber for use in accordance with certain embodiments.

FIGS. 2A and 2B are schematics illustrating side cross-sectional and top views, respectively, of an exemplary growth chamber 200 for use in accordance with embodiments of the present disclosure. The growth chamber 200 includes an upper plate 202 and a lower plate 204 that together enclose an interior volume 206 for culturing and maintaining, for example, one or more *Physarum polycephalum* specimens on an interior surface of the lower plate 204. The upper plate 202 and the lower plate 204 may be formed, for example, from a transparent material, such as glass or a rigid plastic material. The upper plate 202 and the lower plate 204 may fit together, for example, in a mating relationship, and/or may include one or more latches 208 to reversibly couple the upper plate 202 to the lower plate 204. The upper plate 202 includes an air valve 210 to seal off the interior volume 206 or to expose the interior volume 206 to ambient conditions or conditions of a volume in which the growth chamber 200 is enclosed. The upper plate 202 further includes a port 212 that allows access to the interior volume 206. The port 212 may be large enough to allow for a fluid to be supplied to the interior volume 206, and may allow access of a pipette to remove or sample fluid from the interior volume 206. The port 212 may be sealed, for example, using a rubber stopper. In some embodiments, the lower plate 204 includes a solid growth medium 220, such as an agar growth medium. In some embodiments, a warming plate 222 may be included to control the incubation temperature within the interior volume 206.

The growth chamber 200 may further be coupled to a liquid medium reservoir 214, which may include a nutrient-rich liquid growth medium. In some embodiments, the liquid medium reservoir 214 includes a pump, which may be manually controlled or automatically controlled, to deliver the liquid growth medium through a misting manifold 216 and through misting nozzles 218. In embodiments where the pump is automatically controlled, a controller may be utilized to generate timed pulses of mist or to perform continuous misting.

It is to be understood that the growth chamber 200 is not drawn to scale, and may designed to be of any suitable dimensions and may be modified as desired as would be appreciated by those of ordinary skill in the art. For example, a table-top version of the growth chamber 200 may have a horizontal width spanning 10 cm to 50 cm, and may have a height spanning 5 cm to 25 cm. In some embodiments, the growth chamber may be larger, having widths and heights that span 50 cm to 200 cm or larger. In some embodiments, the growth chamber 200 may be designed to include multiple sub-chambers for culturing separate specimens. In some embodiments, the sub-chambers may be isolated. In other embodiments, the growth chamber 200 may be an individual module that couples to a larger system that controls and maintains the condition of the specimen(s) contained therein.

ILLUSTRATIVE EXAMPLES

The following examples are set forth to assist in understanding the disclosure and should not, of course, be construed as specifically limiting the embodiments described and claimed herein. Such variations of the embodiments, including the substitution of all equivalents now known or later developed, which would be within the purview of those skilled in the art, and changes in formulation or minor changes in experimental design, are to be considered to fall within the scope of the embodiments incorporated herein.

Example 1: Preparation of Expression Cassettes for Producing Human Insulin

Figure 3:
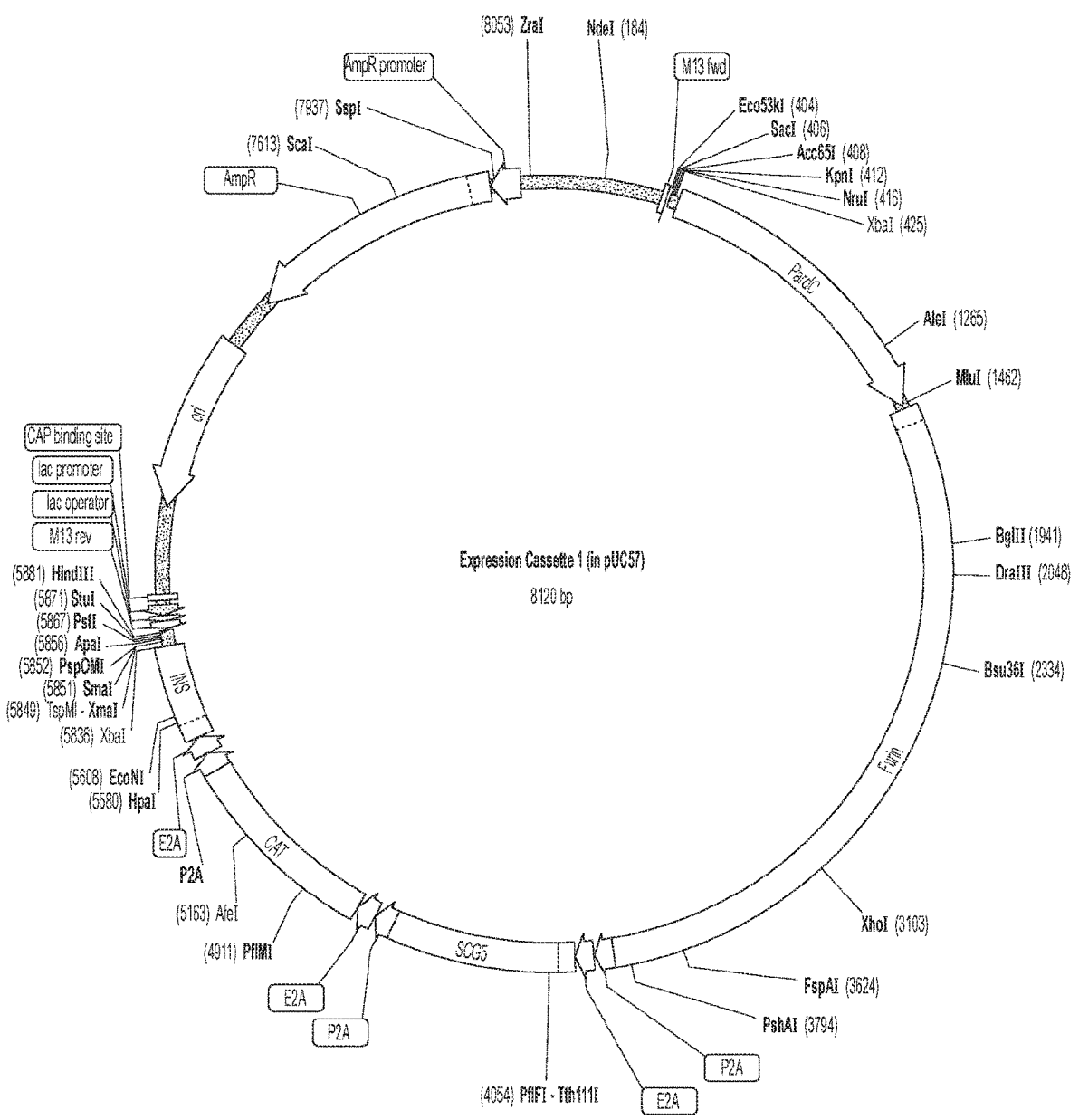
FIG. 3 is a vector map of a first exemplary nucleic acid sequence encoding for furin, neuroendocrine protein 7B2, and preproinsulin in accordance with certain embodiments.
Figure 4:
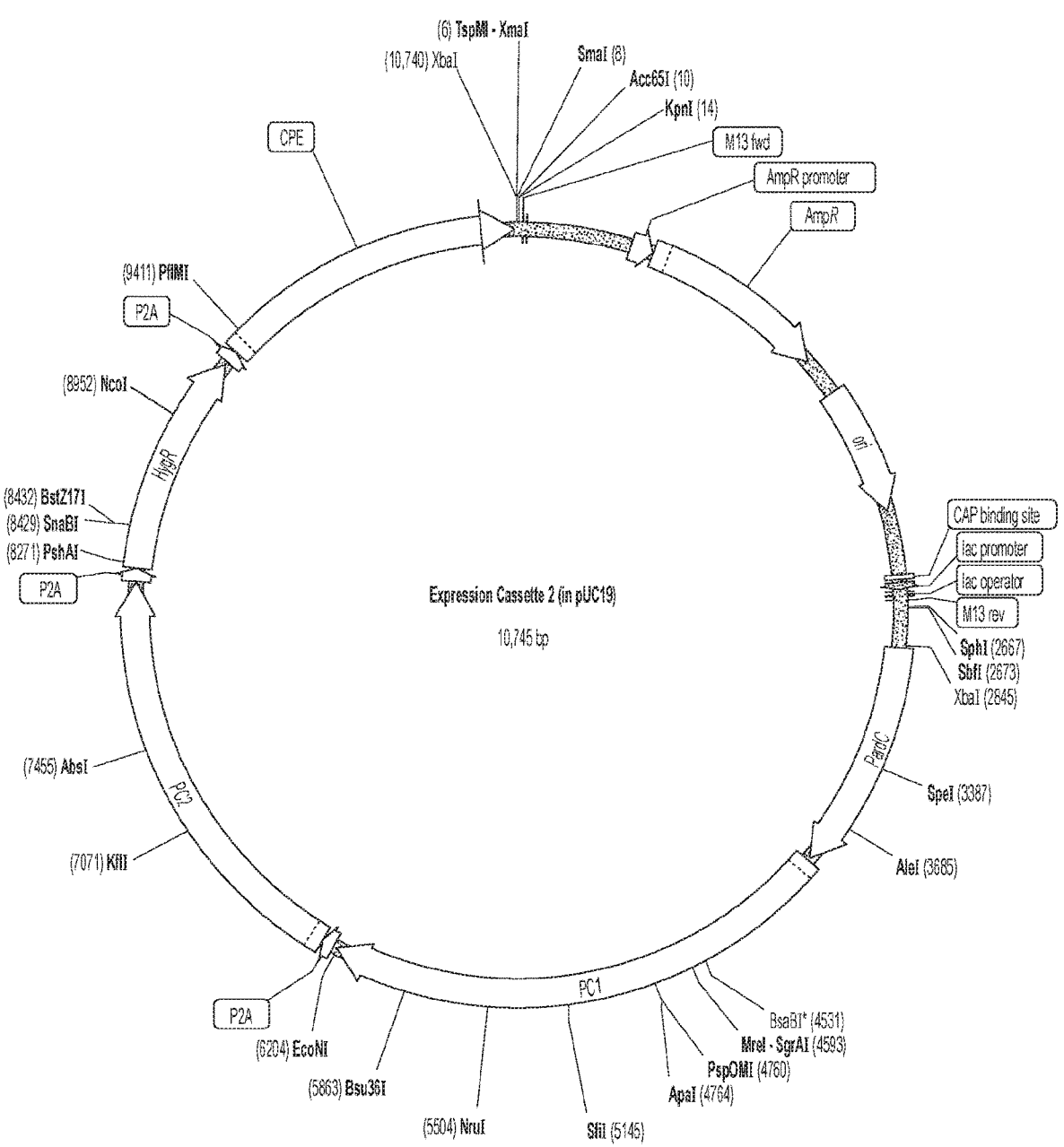
FIG. 4 is a vector map of a second exemplary nucleic acid sequence encoding for proprotein convertase 1, proprotein convertase 2, and carboxypeptidase E in accordance with certain embodiments.

Two expression cassettes were separately prepared. Expression Cassette 1 (SEQ ID NO:1) was prepared in a pUC57 vector, and is summarized in Table 1 below and illustrated as a vector map in FIG. 3. Expression Cassette 2 (SEQ ID NO:2) was prepared in a pUC19 vector, and is summarized in Table 2 below and illustrated as a vector map in FIG. 4.

Prior to transfection, plasmids containing each expression cassette were linearized using an XbaI restriction digestion protocol, where 1 μg of vector plasmid (pUC57 for Expression Cassette 1 and pUC19 for Expression Cassette 2) was mixed together with 5 μL universal buffer (ABM), 10 U XbaI restriction enzyme (ABM), and a volume of molecular biology grade water to bring the total reaction volume to 50 μL. The reaction volume was incubated at 37° C. for 60 minutes. Reaction products were separated using agarose gel electrophoresis, and expression cassette bands were purified with an electrophoresis extraction kit (IBI Scientific) for use in the following transfection protocol.

TABLE 1

Expression Cassette 1 Details

| Segment/ Gene | Nucleotide Sequence | Description/ Encoded Protein |
|---|---|---|
| PardC | 431-1479 of SEQ ID NO: 1 | Transcriptional promoter |
| FURIN | 1480-3840 of SEQ ID NO: 1 | Furin with PsA signal peptide |
| P2A | 3841-3906 of SEQ ID NO: 1 | Self-cleaving peptide |
| E2A | 3907-3975 of SEQ ID NO: 1 | Self-cleaving peptide |
| SCG5 | 3976-4590 of SEQ ID NO: 1 | Neuroendocrine protein 7B2 with PsA signal peptide |
| P2A | 4591-4656 of SEQ ID NO: 1 | Self-cleaving peptide |
| E2A | 4657-4725 of SEQ ID NO: 1 | Self-cleaving peptide |
| CAT | 4726-5382 of SEQ ID NO: 1 | Chloramphenicol acetyltransferase |
| P2A | 5383-5448 of SEQ ID NO: 1 | Self-cleaving peptide |
| E2A | 5449-5517 of SEQ ID NO: 1 | Self-cleaving peptide |
| INS | 5518-5835 of SEQ ID NO: 1 | Preproinsulin with PsA signal peptide |

TABLE 2

Expression Cassette 2 Details

| Segment/ Gene | Nucleotide Sequence | Description/ Encoded Protein |
|---|---|---|
| PardC | 2851-3899 of SEQ ID NO: 2 | Transcriptional promoter |
| PC1 | 3900-6215 of SEQ ID NO: 2 | Proprotein convertase 1 with PsA signal peptide |
| P2A | 6216-6281 of SEQ ID NO: 2 | Self-cleaving peptide |
| PC2 | 6282-8177 of SEQ ID NO: 2 | Proprotein convertase 2 with PsA signal peptide |
| P2A | 8178-8243 of SEQ ID NO: 2 | Self-cleaving peptide |
| HygR | 8244-9266 of SEQ ID NO: 2 | Hygromycin B phosphotransferase |
| P2A | 9267-9332 of SEQ ID NO: 2 | Self-cleaving peptide |
| CPE | 9333-10739 of SEQ ID NO: 2 | Carboxypeptidase E with PsA signal peptide |

Prespore specific protein A (PsA) signal peptide was used as a secretion tag in both expression cassettes to direct the secretion of all target proteins. The antibiotic resistance proteins, namely hygromycin B phosphotransferase and chloramphenicol acetyltransferase, are not tagged for secretion as they function primarily inside the cell.

PsA signal peptide (e.g., gene name pspA, with variants encoded by nucleotide sequences: 1480-1536, 3976-4032, and 5518-5574 of SEQ ID NO:1; and 3900-3956, 6282-6338, and 9333-9389 of SEQ ID NO:2) is known to be a functional and very efficient secretion tag in *Dictyostelium discoideum*. See Dittrich et al., "Production and secretion of recombinant proteins in *Dictyostelium discoideum*," Nat. Biotechnol. 12, pp. 614-618 (1994). At present, it appears that no clearly defined secretion tags are known for *Physarum polycephalum*. It also appears that no data exists on the efficiency of secretion for specific secreted proteins in *Physarum polycephalum*. However, phylogenetic analyses in the late 1990s found that the classes Myxogastria and Dictyostelia evolved from a common ancestor and share similar amino acid and nucleic acid sequence identities (89-97% and 77-92%, respectively). See Baldauf et al., "Origin and evolution of slime molds (Mycetozoa)," Proc. Natl. Acad. Sci. 94, pp. 12007-12012 (1997). These data promoted the belief that *Physarum polycephalum* and *Dictyostelium discoideum*, a more well-studied slime mold, are close molecular relatives even though *Dictyostelium* is a cellular slime mold. Thus, PsA signal peptide was selected for use in these illustrative examples for at least these reasons.

Example 2: Transfection Protocol

A DNA mixture was prepared by mixing 1 μg total of linear DNA (a 1:1 ratio of Expression Cassette 1 and Expression Cassette 2 in their respective linearized plasmids), 30 μL of 10 mM Tris-HCL (IBI Scientific), and 20 μL pH 8 buffer.

A lipofection reagent mixture was prepared by mixing 2 μL of DreamFect™ Gold Transfection Reagent (OZ Biosciences) and 50 μL of a pH 8 buffer.

The DNA mixture and lipofection reagent mixtures were mixed and incubated at room temperature for 20 minutes to form a transfection mixture.

A *Physarum polycephalum plasmodium* specimen (spanning 1 cm$^2$) was submerged in 50 μL of pH 8 buffer in a 1.5 mL microcentrifuge tube. It is preferred that the specimen be transferred on a slice of its growth medium, such as agar. The specimen was pushed to the bottom of the tube without crushing or folding it to avoid damaging the cell.

The transfection mixture was then pipetted into the buffer containing the plasmodium, and the microcentrifuge tube was laid horizontally on its side and incubated at room temperature. At three hour intervals, the tube was momentarily opened every to aerate, and then closed and gently inverted to mix the reaction. These steps are preferred in order to improve survival rates, but may not be necessary if a ventilated tube is used.

At 16 hours post transfection, the tube was inverted on a shallow slant to separate most of the liquid from the specimen slice. This step was performed to discourage the specimen from dissociating into cellular *flagellates*, as *Physarum polycephalum* often does in liquid culture especially when agitated. The specimen was incubated in this position for an additional 4 hours.

At 20 hours post transfection, the specimen was transferred to a solid growth medium for recovery in the presence of oatmeal agar (which is preferred), and incubated at room temperature.

At 42 hours post transfection, 1 cm$^2$ of the transfected specimen was transferred to an oatmeal agar selection plate with the appropriate antibiotic: 1 mg/ml chloramphenicol (MI Scientific) for Expression Cassette 1, or 100 μg/ml hygromycin B (Bio Basic) for Expression Cassette 2. Incubate at room temperature.

For specimens transfected with Expression Cassette 1, negative controls (CAT-negative) did not grow on the selection plate and died within 12 days. CAT-positive clones appeared healthy and grew uninhibited.

Figure 5:
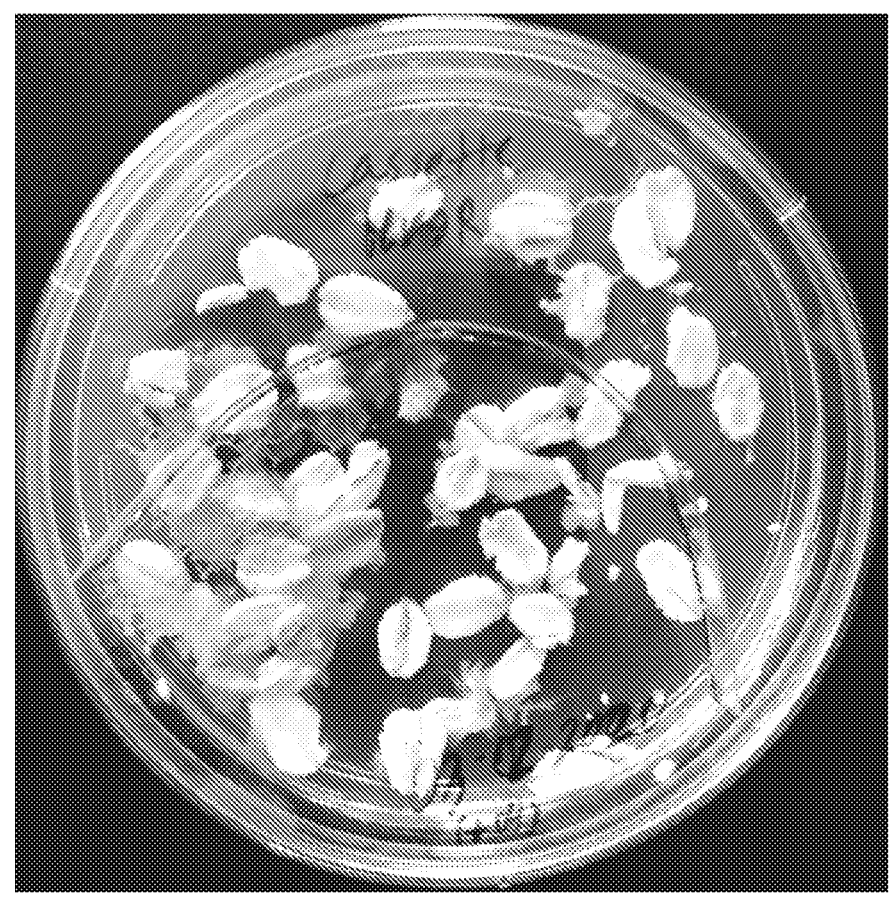
FIG. 5 is a photograph of *Physarum polycelphalum* growing on a selection plate after two successful transfections.

For specimens transfected with Expression Cassette 2, negative controls (HygR-negative) did not grow on the selection plate and died within 48 hours. HygR-positive clones appeared healthy and grew uninhibited. FIG. 5 is a photograph showing HygR-positive clones growing on a selection plate, corresponding to specimens that were successfully transfected with both Expression Cassette 1 and Expression Cassette 2. The specimens are attached to oat flakes and have a web-like appearance.

Hygromycin and chloramphenicol are used here with their respective resistance genes because these selectable markers, at present, are the only two known to be suitable for selection in *Physarum polycephalum*, likely due to the organism's natural resistance to most commonly used selection drugs. It is noted that chloramphenicol is most active on bacterial ribosomes and least active on eukaryotic cytoplasmic ribosomes, however, eukaryotic mitochondrial ribosomes have a sensitivity similar to bacterial ribosomes, so the selection can still take place.

Example 3: Protein Collection

Transfected specimens were rinsed with a pH 6 buffer solution (though a pH range between 5 and 8 could be used with little variation). If only a small sample is needed, such as for verification, this can be obtained by pipetting small volumes of buffer solution up and down on the specimen surface repeatedly while being careful not to puncture the cell membrane. If larger samples are needed, such as for purification and use, these can be obtained by simply misting the specimen with buffer solution until a significant pool forms in the container, or by covering the specimen in a thin layer of buffer solution and draining it off. Collected buffer solution was subjected to ultrafiltration prior to downstream use (e.g. testing, verification, purification, etc.).

Example 4: High Fructose Corn Syrup Enzyme Production (Prophetic Example)

Expression Cassette 3 encoding glucose isomerase (GI) and HPH is contemplated and may be prepared using similar protocols as described above, with similar protocols being used for transfection and protein collection as described above. Expression Cassette 3 is summarized in Table 3 below.

GI converts D-glucose into D-fructose, and originates from the organism *Thermoanaerobacterium saccharolyticum*. This enzyme is used heavily in industry to produce high-fructose corn syrup (HFCS), an important constituent of many foods. As GI is expensive to produce, HFCS manufacturers often put forth great effort to recover or immobilize it for maximum reuse. Expression of GI using the embodiments described herein could provide relief to HFCS suppliers and a subsequent cost reduction for this product.

Expression Cassette 3 is designed for relatively simple selection of desired clones (due to the inclusion of a hygromycin resistance gene) and high production rate (using the PardC promoter). The P2A and E2A self-cleaving peptides ensure that the GI and HPH are produced at the same rate, but do not interfere with each other upon translation. Additionally, a secretion tag, such as the PsA signal peptide derived from *Dictyostelium discoideum*, is added to the N-terminus of GI to facilitate its secretion for ease of harvesting using the rinsing method described above in Example 3. The secretion tag can be omitted if the recombinant protein is to be harvested as inclusion bodies by cell disruption.

TABLE 3

| Expression Cassette for GI Expression | |
| --- | --- |
| Expression Cassette | Description |
| 3 | PardC-GI-P2A-E2A-HPH |

Example 5: Production of Enzymes Used in Cell-Free Glucose Fermentation of Glucose to Ethanol (Prophetic Example)

Expression Cassettes 4-11 encoding various enzymes used in connection with cell-free glucose fermentation are contemplated and may be prepared using similar protocols as described above, with similar protocols being used for transfection and protein collection as described above. Expression Cassettes 4-11 are summarized in Tables 4 and 5 below.

This example highlights the ability of *Physarum polycephalum* to express various proteins in a polycistronic or bicistronic manner. Expression Cassettes 4 and 5 are polycistronic expression cassettes that express eight proteins total after transfection. Expression Cassettes 5-11 are bicistronic expression cassettes that express seven proteins total after transfection.

Six of the proteins in this example facilitate a minimized metabolic pathway meant to convert glucose to ethanol, as described in Guterl et al., "Cell-free metabolic engineering: production of chemicals by minimized reaction cascades," *ChemSusChem* 5, pp. 2165-2172 (2012). The six proteins include: (1) glucose dehydrogenase (GDH) (origin: *Saccharolobus solfataricus*); (2) dihydroxyacid dehydratase (DHAD) (origin: *Saccharolobus solfataricus*); (3) gluconate/galactonate dehydratase (KDGA) (origin: *Sulfolobus acidocaldarius*); (4) glyceraldehyde dehydrogenase (AIHD) (origin: *Thermoplasma acidophilum*); (5) pyruvate decarboxylase (PDC) (origin: *Zymomonas mobilis*); and (6) alcohol dehydrogenase (ADH) (origin: *Geobacillus stearothermophilus*). The other two proteins, HPH and CAT, are used to select for desired clones.

The CAT protein only appears in a polycistronic cassette (Expression Cassette 5) to allow for differentiation between transfection of the Expression Cassettes 4 and 5 (which may be performed sequentially or concurrently as described above in Example 2). Each protein may also be expressed separately in individual *Physarum polycephalum* specimens and combined downstream after purification. For this case, the bicistronic expression cassettes are designed for individual selection with hygromycin. For both the polycistronic and bicistronic expression cassettes, each of the six proteins involved in the metabolic pathway bear a secretion tag, such as the PsA signal peptide derived from *Dictyostelium discoideum*, on their N-termini to facilitate their secretion for ease of harvesting using the rinsing method described above in Example 3. The secretion tag can be omitted if the recombinant protein is to be harvested as inclusion bodies by cell disruption.

TABLE 4

| Polycistronic Expression Cassettes | |
| --- | --- |
| Expression Cassette | Description |
| 4 | PardC-GDH-P2A-E2A-DHAD-P2A-E2A-KDGA-P2A-E2A-HPH |
| 5 | PardC-AIHD-P2A-E2A-PDC-P2A-E2A-ADH-P2A-E2A-CAT |

TABLE 5

| Bicistronic Expression Cassettes | |
| --- | --- |
| Expression Cassette | Description |
| 6 | PardC-HPH-P2A-E2A-GDH |
| 7 | PardC-HPH-P2A-E2A-DHAD |
| 8 | PardC-HPH-P2A-E2A-KDGA |
| 9 | PardC-HPH-P2A-E2A-AIHD |
| 10 | PardC-HPH-P2A-E2A-PDC |
| 11 | PardC-HPH-P2A-E2A-ADH |

Example 6: Production of Antiviral Drug Enfuvirtide (Prophetic Example)

Expression Cassette 12 encoding Enfuvirtide (T20) (origin: Human Immunodeficiency Virus) and HPH is contemplated and may be prepared using similar protocols as described above, with similar protocols being used for transfection and protein collection as described above. Expression Cassette 12 is summarized in Table 6 below.

Enfuvirtide is an HIV fusion inhibitor used widely in combination therapy to treat HIV-1 infections. Expression Cassette 12 is designed for relatively simple selection of desired clones (due to the inclusion of a hygromycin resistance gene) and high production rate (using the PardC promoter). The P2A and E2A self-cleaving peptides ensure that the T20 and HPH are produced at the same rate, but do not interfere with each other upon translation. Additionally, a secretion tag, such as the PsA signal peptide derived from *Dictyostelium discoideum*, is added to the N-terminus of T20 to facilitate its secretion for ease of harvesting using the rinsing method described above in Example 3. The secretion tag can be omitted if the recombinant protein is to be harvested as inclusion bodies by cell disruption.

TABLE 6

| Expression Cassette for T20 Expression | |
| --- | --- |
| Expression Cassette | Description |
| 12 | PardC-HPH-P2A-E2A-T20 |

Example 7: Production of a Commonly Used Protease Enzyme (Prophetic Example)

Expression Cassette 13 encoding subtilisin (apr) (origin: *Bacillus amyloliquefaciens*) and HPH is contemplated and may be prepared using similar protocols as described above, with similar protocols being used for transfection and protein collection as described above. Expression Cassette 13 is summarized in Table 7 below.

Subtilisin is a protease commonly protein-engineered for use in stain elimination and cleaning. Engineered derivatives of subtilisin are used in many laundry and dishwashing detergents, contact lens cleaning solutions, cosmetics, and food processes. Expression Cassette 13 is designed for relatively simple selection of desired clones (due to the inclusion of a hygromycin resistance gene) and high production rate (using the PardC promoter). The P2A and E2A self-cleaving peptides ensure that the apr and HPH are produced at the same rate, but do not interfere with each other upon translation. Additionally, a secretion tag, such as the PsA signal peptide derived from *Dictyostelium discoi-*

*deum*, is added to the N-terminus of apr to facilitate its secretion for ease of harvesting using the rinsing method described above in Example 3. The secretion tag can be omitted if the recombinant protein is to be harvested as inclusion bodies by cell disruption.

TABLE 7

| Expression Cassette for Subtilisin Expression | |
| --- | --- |
| Expression Cassette | Description |
| 13 | PardC-HPH-P2A-E2A-apr |

Example 8: Production of Taq DNA Polymerase (Prophetic Example)

Expression Cassette 14 encoding Taq DNA polymerase (polA) (origin: *Thermus aquaticus*) and HPH is contemplated and may be prepared using similar protocols as described above, with similar protocols being used for transfection and protein collection as described above. Expression Cassette 14 is summarized in Table 8 below.

Taq DNA polymerase is a valuable thermostable DNA polymerase used extensively in both scientific research and clinical diagnostic tests. Expression Cassette 14 is designed for relatively simple selection of desired clones (due to the inclusion of a hygromycin resistance gene) and high production rate (using the PardC promoter). The P2A and E2A self-cleaving peptides ensure that the polA and HPH are produced at the same rate, but do not interfere with each other upon translation. Additionally, a secretion tag, such as the PsA signal peptide derived from *Dictyostelium discoideum*, is added to the N-terminus of polA to facilitate its secretion for ease of harvesting using the rinsing method described above in Example 3. The secretion tag can be omitted if the recombinant protein is to be harvested as inclusion bodies by cell disruption.

TABLE 8

| Expression Cassette for Taq DNA Polymerase Expression | |
| --- | --- |
| Expression Cassette | Description |
| 14 | PardC-HPH-P2A-E2A-polA |

Example 9: Production of a Commonly Used Milk Coagulation Enzyme (Prophetic Example)

Expression Cassette 15 encoding chymosin (CYM) (origin: *Bos taurus*) and HPH is contemplated and may be prepared using similar protocols as described above, with similar protocols being used for transfection and protein collection as described above. Expression Cassette 15 is summarized in Table 9 below.

Chymosin is an enzyme used widely in the dairy product industry (especially cheese production) for the coagulation of milk. Expression Cassette 15 is designed for relatively simple selection of desired clones (due to the inclusion of a hygromycin resistance gene) and high production rate (using the PardC promoter). The P2A and E2A self-cleaving peptides ensure that the CYM and HPH are produced at the same rate, but do not interfere with each other upon translation. Additionally, a secretion tag, such as the PsA signal peptide derived from *Dictyostelium discoideum*, is added to the N-terminus of CYM to facilitate its secretion for ease of harvesting using the rinsing method described above in Example 3. The secretion tag can be omitted if the recombinant protein is to be harvested as inclusion bodies by cell disruption.

TABLE 9

| Expression Cassette for Chymosin Expression | |
|---|---|
| Expression Cassette | Description |
| 15 | PardC-HPH-P2A-E2A-CYM |

Example 10: Production of a Full Human Antibody (Prophetic Example)

Expression Cassette 16 encoding immunoglobulin gamma-1 heavy chain (HC) (origin: *Homo sapiens*) and HPH, and Expression Cassette 17 encoding immunoglobulin lambda-1 light chain (LC) (origin: *Homo sapiens*) and CAT are contemplated and may be prepared using similar protocols as described above, with similar protocols being used for transfection and protein collection as described above. Expression Cassettes 16 and 17 are summarized in Table 10 below.

Antibodies are used widely in research and clinical diagnostic tests, and represent an attractive new therapeutic agent for the treatment of many diseases, including cancer and microbial infections. Efficient production of full antibodies and antibody fragments is paramount to the success of these applications, especially as they continue to be developed and implemented. Expression Cassettes 16 and 17 are designed for relatively simple selection of desired clones (due to the inclusion of a hygromycin resistance gene and chloramphenicol resistance gene, respectively) and high production rate (using the PardC promoter). The disparate resistance genes allow for differentiation between transfection of the Expression Cassettes 16 and 17 (which may be performed sequentially or concurrently as described above in Example 2). Both HC and LC bear a secretion tag, such as the PsA signal peptide derived from *Dictyostelium discoideum*, on their N-termini to facilitate their secretion for ease of harvesting using the rinsing method described above in Example 3. The secretion tag can be omitted if the recombinant protein is to be harvested as inclusion bodies by cell disruption.

The P2A and E2A self-cleaving peptides ensure that each target protein and its respective selection marker are produced at the same rate, but do not interfere with each other upon translation. HC also bears multiple point mutations in its CH domains to allow binding to FcγR in the absence of proper glycosylation, as described in Sazinsky et al., "Aglycosylated immunoglobulin G1 variants productively engage activating Fc receptors," *Proc. Natl. Acad. Sci.* 105(51), pp. 20167-20172 (2008).

TABLE 10

| Expression Cassettes for HC and LC Expression | |
|---|---|
| Expression Cassette | Description |
| 16 | PardC-HPH-P2A-E2A-HC |
| 17 | PardC-CAT-P2A-E2A-LC |

In the foregoing description, numerous specific details are set forth, such as specific materials, dimensions, processes parameters, etc., to provide a thorough understanding of the embodiments of the present disclosure. The particular features, structures, materials, or characteristics may be combined in any suitable manner in one or more embodiments. The words "example" or "exemplary" are used herein to mean serving as an example, instance, or illustration. Any aspect or design described herein as "example" or "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or." That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances. In addition, the use of the terms "a," "an," "the," and similar referents in the context of describing the materials and methods discussed herein (especially in the context of the following claims) are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context.

Reference throughout this specification to "one embodiment," "certain embodiments," "one or more embodiments," "an embodiment," or "some embodiments" means that a particular feature, structure, material, or characteristic described in connection with the embodiment is included in at least one embodiment of the present disclosure. Thus, the appearances of the phrases such as "in one or more embodiments," "in certain embodiments," "in one embodiment," or "in an embodiment" in various places throughout this specification are not necessarily referring to the same embodiment of the present disclosure. Furthermore, the particular features, structures, materials, or characteristics may be combined in any suitable manner in one or more embodiments.

It is to be understood that the above description is intended to be illustrative, and not restrictive. Many other embodiments will be apparent to those of skill in the art upon reading and understanding the above description. The scope of the disclosure should, therefore, be determined with reference to the appended claims, along with the full scope of equivalents to which such claims are entitled. The use of any and all examples, or exemplary language (e.g., "such as") provided herein, is intended merely to illuminate certain materials and methods and does not pose a limitation on scope. No language in the specification should be construed as indicating any non-claimed element as essential to the practice of the disclosed materials and methods.

Although the embodiments disclosed herein have been described with reference to particular embodiments it is to be understood that these embodiments are merely illustrative of the principles and applications of the present disclosure. It will be apparent to those skilled in the art that various modifications and variations can be made to the method and apparatus of the present disclosure without departing from the spirit and scope of the disclosure. Thus, it is intended that the present disclosure include modifications and variations that are within the scope of the appended claims and their equivalents, and the above-described embodiments are presented for purposes of illustration and not of limitation.

What is claimed is:

1. A system for protein production comprising:

a growth chamber; and multinucleate plasmodia of *Physarum polycephalum* disposed within the growth chamber, wherein the *Physarum polycephalum* is modified to comprise a nucleic acid sequence having at least 90% sequence identity to SEQ ID NO: 1 or SEQ ID NO:2 that, when expressed by the *Physarum polycephalum*, results in the production of one or more recombinant proteins encoded by the nucleic acid sequence, wherein the one or more recombinant proteins are expressed with a secretion tag, and wherein the growth chamber comprises a port to allow removal of fluid containing the one or more recombinant proteins; and wherein the one or more recombinant proteins are selected from one or more of glucose isomerase, glucose dehydrogenase, dihydroxyacid dehydratase, gluconate/galactonate dehydratase, glyceraldehyde dehydrogenase, pyruvate decarboxylase, alcohol dehydrogenase, functional variants thereof, or combinations thereof.

2. *Physarum polycephalum* modified to produce a metabolic enzyme or a functional variant thereof having enzyme activity.

3. The system of claim 1, wherein the multinucleate plasmodia are macroplasmodia.

4. The system of claim 1, wherein the nucleic acid sequence is chromosomally-integrated into the *Physarum polycephalum*.

5. The system of claim 1, wherein the *Physarum polycephalum* is diploid when in the form of the multinucleate plasmodia.

6. The system of claim 1, wherein the one or more recombinant proteins comprise a metabolic enzyme or a functional variant thereof.

7. The system of claim 1, wherein the nucleic acid sequence encodes for glucose isomerase, dihydroxyacid dehydratase, gluconate/galactonate dehydratase, glyceraldehyde dehydrogenase, pyruvate decarboxylase, alcohol dehydrogenase, functional variants thereof, or combinations thereof.

8. The *Physarum polycephalum* of claim 2, in a form of macroplasmodia.

9. The *Physarum polycephalum* of claim 2, comprising a nucleic acid sequence encoding the metabolic enzyme or the functional variant thereof, wherein the nucleic acid sequence is chromosomally-integrated into the *Physarum polycephalum*.

10. The *Physarum polycephalum* of claim 2, wherein the metabolic enzyme is selected from glucose isomerase, glucose dehydrogenase, dihydroxyacid dehydratase, gluconate/galactonate dehydratase, glyceraldehyde dehydrogenase, pyruvate decarboxylase, alcohol dehydrogenase, functional variants thereof, or combinations thereof.

11. A system for protein production comprising: a growth chamber; and multinucleate plasmodia of *Physarum polycephalum* disposed within the growth chamber, wherein the *Physarum polycephalum* is modified to comprise a nucleic acid sequence having at least 90% sequence identity to SEQ ID NO:1 or SEQ ID NO:2 that, when expressed by the *Physarum polycephalum*, results in the production of one or more recombinant proteins, wherein the one or more recombinant proteins is selected from glucose isomerase, dihydroxyacid dehydratase, gluconate/galactonate dehydratase, glyceraldehyde dehydrogenase, pyruvate decarboxylase, alcohol dehydrogenase, functional variants thereof, or combinations thereof.

12. The system of claim 1, wherein the nucleic acid sequence comprises SEQ ID NO: 1 or SEQ ID NO:2.

13. The system of claim 1, wherein the secretion tag is a prespore specific protein A (PsA) signal peptide.

14. The system of claim 1, wherein the secretion tag is native to *Dictyostelium discoideum*.

* * * * *

SEQUENCE LISTING

```
<160> NUMBER OF SEQ ID NOS: 2

<210> SEQ ID NO 1
<211> LENGTH: 8120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta cgccagggt     360 tttcccagtc acgacgttgt aaaacgacgg ccagtgaatt cgagctcggt acctcgcgaa     420
tgcatctaga ggatctccac actattgcac atgctaccgt aatcaattat aggccgaaat     480
cactctatca actcaccccg agcggtgtac actcactcca ctcacaatca cacttaatca     540
catcttcacc ttgttcattt gtgcatgttt actagcgcat gttcgcccca catgctcaca     600
atcatcactc cactcactct tggcgctagc cattacatac cttgaattag caaaacttta     660
cgcaaatgta gctagagaat gagtacaaag gggaaggaa gtaataagtg aaagtggaat     720
ggaaaatggg caatgggaaa cgtggttagg gatgtatgtg gctaggatat ggataggacg     780
tattggggag ggagtgatag gatagaggat atggtatgac agtgcgagcg tgatatatga     840
gacatgtagc tagtaagccg gagggaagga taaaatcaca aggggagtat aaagggagga     900
agtacaacaa caatacaaca agaaaacatg gactatgaga tgaaaaacat tgtgtgctta     960
tgtagaacta gttaaaaaca cggacaaaaa ggtgaacaaa tacgattaga acacatacag    1020
aggcggtaca acaacaaagc aacaagagaa aatgtgagat tctgaaatga gaacgaggag    1080
aaggacgatc agctaagtga tggagtggaa aagttatgat atgggaaaa aacacggata    1140 gaaaggtgaa gctatagaga catgaaggga aagcaaaaac aaagaaaaaa catgcggttc    1200
tgaaatgaga atgggggaga agggcaatca gctaagtgat ggaggagaag ttagtgctgg    1260
cacgttggtg aagagcgccc ccagacctgt ggaccggcat ttacgcacgt tttacgcacg    1320
atttacgcca aattttcgga gcggttgcga aatttgcctt ttcggggtaa aatttacaca    1380
acttttacgc acttttttcgg ttctgatttt tgcattggca ggtgcgaaat gattggggag    1440
tggaacagat aaaaggtga aacgcgtcgc tcttctttga tgaaattcca acatacattt    1500
atagccttgt tatcgctgct tacatacgca aatgctcaga aggttttac taacacctgg    1560 gcggtgcgga taccgggggg gccagccgtt gccaatagcg tcgcacgtaa acacgggttt    1620
ctaaacctgg gtcagatatt tggagattac taccacttct ggcatagagg ggtgacaaag    1680
aggtccctct ctcctcaccg gcctaggcac tcaaggctac agagggaacc ccaagtgcaa    1740
tggctggaac aacaagtagc caaacgccgc acgaagcgag atgtatacca agagcccacg    1800
gaccctaaat tcccccaaca atggtacttg agtggggtga cgcagcgaga cctcaacgta    1860
```

-continued

```
aaagccgcct gggcgcaagg atataccggt catggtattg tcgtgtcgat tctggacgac   1920
gggatcgaaa agaatcaccc agatctagcg ggaaattacg atcccggagc atccttcgac   1980
gtaaacgatc aggatccaga tccgcaacct aggtatacac aaatgaatga taaccgacat   2040
ggcaccaggt gcgccggaga ggtggcggcc gtggctaaca acggtgtgtg cggcgttgga   2100
gtggcctata acgccagaat cggcggtgtc cgtatgctcg atggtgaagt taccgatgca   2160
gtggaagccc gctctctagg gctcaaccct aatcacattc atatctactc tgcgtcctgg   2220
ggacctgaag atgacggtaa gacagttgac ggacccgcga gattggcgga agaagcattt   2280
ttccgcggag taagccaagg aagaggaggt ttaggcagca tttttcgtctg ggcctcaggt   2340 aacggaggtc gtgagcacga ctcgtgcaat tgtgacggtt atacaaactc tatctatact   2400
ttgtccatta gctccgcgac acaattcgga aacgttccat ggtactcgga ggcttgctct   2460
agcacgctcg ccactacata tagctcaggc aatcaaaacg agaaacagat cgtcaccact   2520
gatcttagac agaagtgtac ggagagtcac acaggcacga gtgcttcagc gcccttagct   2580
gccggcatta tcgcattaac tcttgaggca aacaagaatc ttacgtggag agatatgcag   2640
catctggttc tccaaacaag caaaccagcc catcttaacg caaacgactg ggctacaaac   2700
ggagtgggtc gtaaagtcag tcattcctat ggttacggat tacttgacgc gggagctatg   2760
gttgcactcg cccaaaactg gaccacagtt gcccccccaac gcaaatgcat tattgatatc   2820
cttacagagc caaaggacat tggaaaaaga ttggaggtca gaaagactgt gactgcttgc   2880
ctgggagaac ctaatcacat caccgtctc gaacacgcgc aggctcgttt aactctttcc   2940
tacaatcgcc gcggagacct ggcaatccac ctggtttctc ctatgggaac ccgttccaca   3000
ctcctggctg ctcgcccgca cgattactcc gcggatggct ttaatgattg ggcttttatg   3060
actactcact cctgggacga ggaccctcc ggagaatggg tcctcgagat cgagaacacc   3120
tcggaggcga acaattacgg aactcttact aagttcactt tggttctcta cggcactgca   3180
ccggagggcc tcccagttcc gcctgagtca agcggatgca agacctcac tagtagccaa   3240 gcctgcgttg tgtgcgaaga gggcttctct ttgcaccaga agtcgtgcgt gcagcactgc   3300
cctcctggat tcgctccaca ggtcttggac acccactaca gtaccgagaa tgatgtagaa   3360
accatccgtg ctagcgtgtg tgctccttgc cacgcctcct gtgccacctg ccagggacca   3420
gctcttaccg attgtttgtc ttgcccatca cacgcctctt tggatcccgt ggagcaaacc   3480
tgttcccgtc agtctcaaag ctcacgtgaa tctcccccac aacaacagcc ccccgcttg   3540 ccacccgagg tagaagcagg acaacgcctc cgcgccggcc tcctccctc acacttgccc   3600 gaggttgtag ctggcctctc gtgcgcattc atcgtccttg tttttgtgac cgtcttcctc   3660
gtgctccaac tccgctccgg cttctctttc cgcggagtaa aggtctacac catggaccgc   3720
ggcttgatct cttacaaggg tctccccca gaggcatggc aggaagagtg tccctccgac   3780
tccgaagagg acgagggtcg cggtgaacgc accgctttca ttaaggacca gtccgcattg   3840
ggatccggag caaccaactt ctctcttttg aagcaagctg agacgtggga ggagaacccc   3900
ggacccggtt ctggacaatg caccaactac gctttgttga agttggctgg agacgtggag   3960
tctaaccccg gtcccatgaa gttccaacac acattccatg ccttgttaag cctactaaca   4020
tacgctaacg cctacagccc ccgcaccca gaccgcgtca gtgaggcaga tattcagcgt   4080
ttgttacatg gcgtcatgga gcagctcggc atcgccagac cgcgtgtcga atatccggcc   4140
caccaagcta tgaatcttgt tggcccacag tccattgaag gtggagcaca cgaagggctt   4200
```

-continued

```
caacatctcg gaccattcgg aaacatcccc aacatcgtgg cagaacttac tggtgataac   4260
attccaaagg atttctctga ggatcaggga tatccagatc cccctaatcc atgccctgtt   4320
ggcaaaaccg ctgacgacgg ttgccttgag aatacccctg acacggccga attttcgagg   4380
gagttccagc tgcatcaaca cctgtttgac cccgagcacg actacctctgg gctgggcaaa   4440 tggaacaaaa aactcctcta cgagaaaatg aagggggggag aaaggcgcaa gcgccgatca   4500
gtgaacccct acttgcaagg tcaaagattg gataacgttg tagcgaagaa gtctgtgcct   4560
cacttttccg atgaggacaa ggaccccgag ggatctggag ctaccaattt ctcactcctc   4620
aagcaagcgg gtgacgtaga ggagaatccc ggacccggat ccggtcaatg tactaactac   4680
gctttgctca agttggcggg agatgtggaa tccaacccccg gacccatgga gaaaaaaatt   4740
accggttaca caaccgtcga catttcacaa tggcaccgta aagagcactt tgaagcattt   4800
caatctgtag ctcaatgtac atataaccag accgttcaat tggacataac agctttttg   4860 aagacggtaa aaaagaataa acacaagttc taccccgcat tcatccatat tctggccaga   4920
ttgatgaacg ctcacccgga attcaggatg gccatgaagg atggagagct agtcatttgg   4980
gattctgtcc acccttgcta cacagtcttt catgaacaga cggagaccct cagctcatta   5040
tggagtgagt atcacgatga cttttcgccaa ttcctgcaca tctactctca ggacgtagct   5100
tgttacgggg aaaatttggc gtacttccca aagggattta tcgaaaatat gttttctcgtt   5160 agcgctaacc cctgggtgtc cttcacctcc ttcgatttaa atgttgctaa catggataac   5220
ttcttcgcgc ccgtgttcac tatgggtaag tattatactc aggggggacaa ggtgcttatg   5280 cctcttgcaa tccaggttca tcacgcggtt tgcgacggat tccacgtggg tcgcatgctt   5340
aatgagttgc aacaatactg cgacgaatgg cagggtggag caggctccgg cgccactaac   5400
ttctccctcc tcaagcaagc cggcgatgtg gaggagaacc caggcccagg atcgggacaa   5460
tgcactaact acgccctcct caagctcgcc ggagatgtgg agtcgaaccc cggacctatg   5520 aagtccagc atacatttat tgccttactt tccctcctta cctacgctaa tgctttcgtt   5580
aaccaacacc tttgcggcag ccacctggta gaggccctct acctggtttg cggcgagcgc   5640 ggattttttct acacccctaa gactagaagg gaggcagaag acctacaggt ggggcaggtg   5700
gaactcggtg gaggaccagg agcgggttct ttgcaacccc tcgcactcga aggttcgttg   5760
caaaaacgtg gaatcgtcga gcaatgttgc acgtcaatct gttccttgta tcaattggag   5820
aactattgca actaatctag aatcggatcc cgggcccgtc gactgcagag gcctgcatgc   5880
aagcttggcg taatcatggt catagctgtt tcctgtgtga aattgttatc cgctcacaat   5940
tccacacaac atacgagccg gaagcataaa gtgtaaagcc tggggtgcct aatgagtgag   6000
ctaactcaca ttaattgcgt tgcgctcact gcccgctttc cagtcgggaa acctgtcgtg   6060
ccagctgcat taatgaatcg gccaacgcgc ggggagaggc ggtttgcgta ttgggcgctc   6120
ttccgcttcc tcgctcactg actcgctgcg ctcggtcgtt cggctgcggc gagcggtatc   6180
agctcactca aaggcggtaa tacggttatc cacagaatca ggggataacg caggaaagaa   6240
catgtgagca aaaggccagc aaaaggccag gaaccgtaaa aaggccgcgt tgctggcgtt   6300
tttccatagg ctccgccccc ctgacgagca tcacaaaaat cgacgctcaa gtcagaggtg   6360
gcgaaacccg acaggactat aaagatacca ggcgtttccc cctggaagct ccctcgtgcg   6420
ctctcctgtt ccgaccctgc cgcttaccgg atacctgtcc gcctttctcc cttcgggaag   6480
cgtggcgctt tctcatagct cacgctgtag gtatctcagt tcggtgtagg tcgttcgctc   6540
caagctgggc tgtgtgcacg aaccccccgt tcagcccgac cgctgcgcct tatccggtaa   6600
```

```
ctatcgtctt gagtccaacc cggtaagaca cgacttatcg ccactggcag cagccactgg      6660
taacaggatt agcagagcga ggtatgtagg cggtgctaca gagttcttga agtggtggcc      6720
taactacggc tacactagaa gaacagtatt tggtatctgc gctctgctga agccagttac      6780
cttcggaaaa agagttggta gctcttgatc cggcaaacaa accaccgctg gtagcggtgg      6840
tttttttgtt tgcaagcagc agattacgcg cagaaaaaaa ggatctcaag aagatccttt      6900
gatcttttct acggggtctg acgctcagtg gaacgaaaac tcacgttaag ggattttggt      6960
catgagatta tcaaaaagga tcttcaccta gatccttta aattaaaaat gaagttttaa      7020
atcaatctaa agtatatatg agtaaacttg gtctgacagt taccaatgct taatcagtga      7080
ggcacctatc tcagcgatct gtctatttcg ttcatccata gttgcctgac tccccgtcgt      7140
gtagataact acgatacggg agggcttacc atctggcccc agtgctgcaa tgataccgcg      7200
agatccacgc tcaccggctc cagatttatc agcaataaac cagccagccg gaagggccga      7260
gcgcagaagt ggtcctgcaa ctttatccgc ctccatccag tctattaatt gttgccggga      7320
agctagagta agtagttcgc cagttaatag tttgcgcaac gttgttgcca ttgctacagg      7380
catcgtggtg tcacgctcgt cgtttggtat ggcttcattc agctccggtt cccaacgatc      7440
aaggcgagtt acatgatccc ccatgttgtg caaaaaagcg gttagctcct tcggtcctcc      7500
gatcgttgtc agaagtaagt tggccgcagt gttatcactc atggttatgg cagcactgca      7560
taattctctt actgtcatgc catccgtaag atgcttttct gtgactggtg agtactcaac      7620
caagtcattc tgagaatagt gtatgcggcg accgagttgc tcttgcccgg cgtcaatacg      7680
ggataatacc gcgccacata gcagaacttt aaaagtgctc atcattggaa aacgttcttc      7740
ggggcgaaaa ctctcaagga tcttaccgct gttgagatcc agttcgatgt aacccactcg      7800
tgcacccaac tgatcttcag catcttttac tttcaccagc gtttctgggt gagcaaaaac      7860
aggaaggcaa aatgccgcaa aaaagggaat aagggcgaca cggaaatgtt gaatactcat      7920
actcttcctt tttcaatatt attgaagcat ttatcagggt tattgtctca tgagcggata      7980
catatttgaa tgtatttaga aaataaaca aataggggtt ccgcgcacat ttccccgaaa      8040
agtgccacct gacgtctaag aaaccattat tatcatgaca ttaacctata aaaataggcg      8100
tatcacgagg ccctttcgtc                                                 8120
```

<210> SEQ ID NO 2
<211> LENGTH: 10745
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2

```
ggatccccgg gtaccgagct cgaattcact ggccgtcgtt ttacaacgtc gtgactggga        60
aaaccctggc gttacccaac ttaatcgcct tgcagcacat ccccctttcg ccagctggcg       120
taatagcgaa gaggcccgca ccgatcgccc ttcccaacag ttgcgcagcc tgaatggcga       180
atggcgcctg atgcggtatt ttctccttac gcatctgtgc ggtatttcac accgcatatg       240
gtgcactctc agtacaatct gctctgatgc cgcatagtta agccagcccc gacacccgcc       300
aacacccgct gacgcgccct gacgggcttg tctgctcccg gcatccgctt acagacaagc       360
tgtgaccgtc tccgggagct gcatgtgtca gaggttttca ccgtcatcac cgaaacgcgc       420
gagacgaaag ggcctcgtga tacgcctatt tttataggtt aatgtcatga taataatggt       480
```

-continued

```
ttcttagacg tcaggtggca ctttttcgggg aaatgtgcgc ggaaccccta tttgtttatt      540
tttctaaata cattcaaata tgtatccgct catgagacaa taaccctgat aaatgcttca      600
ataatattga aaaaggaaga gtatgagtat tcaacatttc cgtgtcgccc ttattccctt      660
ttttgcggca ttttgccttc ctgtttttgc tcacccagaa acgctggtga agtaaaaga      720 tgctgaagat cagttgggtg cacgagtggg ttacatcgaa ctggatctca acagcggtaa      780
gatccttgag agttttcgcc ccgaagaacg ttttccaatg atgagcactt ttaaagttct      840
gctatgtggc gcggtattat cccgtattga cgccgggcaa gagcaactcg gtcgccgcat      900
acactattct cagaatgact tggttgagta ctcaccagtc acagaaaagc atcttacgga      960
tggcatgaca gtaagagaat tatgcagtgc tgccataacc atgagtgata acactgcggc     1020
caacttactt ctgacaacga tcggaggacc gaaggagcta accgcttttt tgcacaacat     1080
gggggatcat gtaactcgcc ttgatcgttg ggaaccggag ctgaatgaag ccataccaaa     1140
cgacgagcgt gacaccacga tgcctgtagc aatggcaaca acgttgcgca aactattaac     1200
tggcgaacta cttactctag cttcccggca acaattaata gactggatgg aggcggataa     1260
agttgcagga ccacttctgc gctcggccct tccggctggc tggtttattg ctgataaatc     1320
tggagccggt gagcgtgggt ctcgcggtat cattgcagca ctggggccag atggtaagcc     1380
ctcccgtatc gtagttatct acacgacggg gagtcaggca actatggatg aacgaaatag     1440
acagatcgct gagataggtg cctcactgat taagcattgg taactgtcag accaagttta     1500
ctcatatata ctttagattg atttaaaact tcattttaa tttaaaagga tctaggtgaa     1560 gatcctttttt gataatctca tgaccaaaat cccttaacgt gagttttcgt tccactgagc     1620
gtcagacccc gtagaaaaga tcaaaggatc ttcttgagat ccttttttttc tgcgcgtaat     1680 ctgctgcttg caaacaaaaa aaccaccgct accagcggtg gtttgtttgc cggatcaaga     1740
gctaccaact cttttttccga aggtaactgg cttcagcaga gcgcagatac caaatactgt     1800
tcttctagtg tagccgtagt taggccacca cttcaagaac tctgtagcac cgcctacata     1860
cctcgctctg ctaatcctgt taccagtggc tgctgccagt ggcgataagt cgtgtcttac     1920
cgggttggac tcaagacgat agttaccgga taaggcgcag cggtcgggct gaacggggggg     1980 ttcgtgcaca cagcccagct tggagcgaac gacctacacc gaactgagat acctacagcg     2040
tgagctatga gaaagcgcca cgcttcccga agggagaaag gcggacaggt atccggtaag     2100
cggcagggtc ggaacaggag agcgcacgag ggagcttcca gggggaaacg cctggtatct     2160
ttatagtcct gtcgggtttc gccacctctg acttgagcgt cgatttttgt gatgctcgtc     2220
aggggggcgg agcctatgga aaaacgccag caacgcggcc tttttacggt tcctggcctt     2280
ttgctggcct tttgctcaca tgttctttcc tgcgttatcc cctgattctg tggataaccg     2340
tattaccgcc tttgagtgag ctgataccgc tcgccgcagc cgaacgaccg agcgcagcga     2400
gtcagtgagc gaggaagcgg aagagcgccc aatacgcaaa ccgcctctcc ccgcgcgttg     2460
gccgattcat taatgcagct ggcacgacag gtttcccgac tggaaagcgg gcagtgagcg     2520
caacgcaatt aatgtgagtt agctcactca ttaggcaccc caggctttac actttatgct     2580
tccggctcgt atgttgtgtg gaattgtgag cggataacaa tttcacacag gaaacagcta     2640
tgaccatgat tacgccaagc ttgcatgcct gcaggtcgac ccgattaagc acagtacctt     2700
tacgttatat ataggattgg tgtttagctt ttttttcctga gccccctggtt gacttgtgca     2760 tgaacacgag ccatttttag tttgtttaag ggaagttttt tgccacccaa aacgtttaaa     2820
```

-continued

```
gaaggaaaag ttgtttctta aacctctaga ggatctccac actattgcac atgctaccgt      2880
aatcaattat aggccgaaat cactctatca actcaccccg agcggtgtac actcactcca      2940
ctcacaatca cacttaatca catcttcacc ttgttcattt gtgcatgttt actagcgcat      3000
gttcgcccca catgctcaca atcatcactc cactcactct tggcgctagc cattacatac      3060
cttgaattag caaaacttta cgcaaatgta gctagagaat gagtacaaag gggaaaggaa      3120
gtaataagtg aaagtggaat ggaaaatggg caatgggaaa cgtggttagg gatgtatgtg      3180
gctaggatat ggataggacg tattgggggag ggagtgatag gatagaggat atggtatgac      3240
agtgcgagcg tgatatatga gacatgtagc tagtaagccg gagggaagga taaaatcaca      3300
aggggagtat aaagggagga agtacaacaa caatacaaca agaaacatg gactatgaga      3360 tgaaaaacat tgtgtgctta tgtagaacta gttaaaaaca cggacaaaaa ggtgaacaaa      3420
tacgattaga acacatacag aggcggtaca acaacaaagc aacaagagaa aatgtgagat      3480
tctgaaatga gaacgaggag aaggacgatc agctaagtga tggagtggaa aagttatgat      3540
atggggaaaa aacacggata gaaaggtgaa gctatagaga catgaaggga aagcaaaaac      3600
aaagaaaaaa catgcggttc tgaaatgaga atgggggaga agggcaatca gctaagtgat      3660
ggaggagaag ttagtgctgg cacgttggtg aagagcgccc ccagacctgt ggaccggcat      3720
ttacgcacgt tttacgcacg atttacgcca aattttcgga gcggttgcga aatttgcctt      3780
ttcggggtaa aatttacaca acttttacgc actttttcgg ttctgatttt tgcattggca      3840
ggtgcgaaat gattggggag tggaacagat aaaagggtga aacgcgtcgc tcttctttga      3900
tgaaattcca gcatacgttt atagctctcc tatcactact aacatacgca aatgcgatgg      3960
aaagaagagc ttggtcctta caatgcacgg cttccgtact cttctgcgca tggtgcgcct      4020
taaattcagc gaaggcaaag aggcagtttg taaacgagtg ggccgccgag attcctggtg      4080
ggccggaagc ggcgtcagca atcgcagagg aattggggta cgacttactc ggtcagatcg      4140
gctcgctgga gaaccattat ctgttcaaac acaagaatca tcctcgtcgt agtagacgct      4200
cggcctttca tattaccaag cgcttatctg atgacgaccg ggtgatttgg gctgaacaac      4260
agtatgaaaa ggaaaggagt aagaggtcag cgctgcgaga ctcagccttg aacctgttta      4320
atgatcctat gtggaatcag cagtggtatc tacaagatac acgtatgact gctgcccttc      4380
cgaagctcga tctgcacgtg atccccgtct ggcagaaggg tatcacaggg aagggtgttg      4440
tcataaccgt cctggacgac ggcctagagt ggaatcacac agatatctat gctaattatg      4500
atcccgaagc gtcatatgat ttcaacgata acgatcacga ccccttcccc cgttatgacc      4560
cgacgaacga aaataagcac ggtacaagat gcgccggcga aatcgccatg caagccaata      4620
accataaatg tggcgttggg gttgcctata attcaaaggt gggcggcatc aggatgctag      4680
acgggatcgt aacggatgca attgaagcct cgagcattgg tttcaacccc ggacacgtgg      4740
atatctacag tgccagctgg ggccccaatg atgatggtaa daccgtggag ggacctggtc      4800
ggctagcgca aaaggccttt gagtatgggg ttaaacaagg gcgacagggg aaaggttcaa      4860
ttttcgtttg ggcctcgggg aacggggggc gacaaggcga caattgcgat tgtgacggtt      4920
ataccgactc tatttacact atctcgatat catcagcaag tcaacaaggt ctttctccct      4980
ggtacgcaga gaagtgctct tctacattag caacgtccta ttcctccggt gactataccg      5040
accagaggat cacatccgcg gatcttcaca acgactgcac tgagacccac acagggacgt      5100
cagcctcagc cccctggca gccgggattt ttgctttggc cctagaggcc aatcccaact      5160
taacttggcg cgatatgcaa cacttggtgg tatggacatc cgagtatgat ccactcgcta      5220
```

-continued

```
acaacccagg atggaagaaa aatggcgcgg gcttgatggt gaattcgaga tttggattcg   5280
gcctactaaa tgcgaaggct ctagtcgact tggctgaccc aagaacgtgg cgcagcgtcc   5340
ccgagaagaa ggaatgcgtt gtcaaagaca atgatttcga gcctcgggcc ttaaaggcaa   5400
atggtgaagt tatcattgag atccccactc gcgcgtgtga gggccaagaa aatgccatta   5460
aatccctgga acatgttcag ttcgaggcta ctattgagta ctcgcgacgc ggcgaccttc   5520
acgtgacgtt aacttccgcg gcggggacgt ccactgtcct cttagctgag cgcgaacgag   5580
atacgtcgcc gaacgggttt aaaaactggg actttatgtc cgttcacact tggggcgaga   5640
atccgattgg cacctggact cttcgaatca ccgacatgtc ggggaggata caaaacgaag   5700
gaaggattgt gaattggaaa ctgattttac atgggaccag ttctcagcct gagcatatga   5760
aacagccaag agtgtacacc tcctataata ctgtacagaa tgacagacgt ggcgtagaaa   5820
agatggttga ccctggtgag gagcaaccga ctcaggaaaa tcctaaggaa aatacgttag   5880
ttagcaagtc accctcatcg agttcagtgg ggggtcgacg ggacgagtta gaggagggcg   5940
ctccgtcaca agctatgttg cgcttacttc agtctgcctt ctccaaaaat agtccgccga   6000
agcaatcgcc gaaaaaaagc ccctccgcaa agcttaatat tccatacgaa aacttttacg   6060
aagccctgga aaaactcaac aagccttcgc agctcaaaga tagtgaggat agtttatata   6120
atgactacgt tgatgtattt tacaacacca agccttacaa gcaccgtgac gacagactgt   6180
tgcaggcatt ggtagatatc cttaacgagg aaaacggttc aggtgctaca aacttttcac   6240
tgttgaagca ggcaggagac gttgaagaaa atccaggtcc tatgaagttc cagcacacgt   6300
tcatagctct gttatcgctc ttgacttatg caaacgctga aaggcctgtt ttcacgaatc   6360
attttcttgt agagctgcat aaaggcggtg aagacaaagc tcgtcaagtc gcagctgagc   6420
atggctttgg tgtccgtaag ctcccttttcg cggagggatt atatcacttc tatcataacg   6480
gactcgccaa ggcgaagcgt cgtcgaagtc tgcatcataa acagcagctt gaaagagatc   6540
ccagagtcaa aatggctctg caacaagaag gctttgaccg caagaagagg ggatataggg   6600
atataaacga aatagatatt aatatgaatg atcccttgtt tacaaagcag tggtatttga   6660
tcaatactgg tcaagcggac ggaacacccg gattggatct taatgtcgcc gaggcctggg   6720
aactgggcta tacgggcaag gggagtgacca ttggaatcat ggacgacgga atcgattatt   6780
tgcatcctga ccttgctagc aactataacg ccgaagcgag ttacgatttt tcaagcaacg   6840
atccttaccc ttacccacgc tacactgatg actggtttaa ttctcacggc acgaggtgcg   6900
ccggagaagt aagtgcggcg gctaacaata acatttgtgg cgtcggtgta gcatataatt   6960
caaaagtggc cggcattcgt atgcttgatc aaccattcat gaccgatatt attgaggcta   7020
gctcgattag tcatatgccc cagctcattg acatctattc tgcgtcctgg ggacccaccg   7080
acaacggcaa gacagtagat ggacctcgtg agctgacatt gcaagctatg gctgatggag   7140
tcaataaagg cagaggtggc aagggtagca tttacgtctg ggccagtggt gatggcggaa   7200
gttacgatga ttgtaattgc gatggctacg ctagctctat gtggactatt tccatcaatt   7260
ctgcgatcaa cgacggtcgc acagcgttgt acgacgaatc ttgctcttct actctggcaa   7320
gcacattctc taatggtagg aaacgcaatc ccgaggctgg tgttgccact accgacctct   7380
acggaaattg taccttgcgc cactcgggaa cctctgcggc ggcccccgag gcggcgggag   7440
tatttgctct tgccctcgag gctaacctcg gcttgacctg gcgtgacatg cagcacctca   7500
ccgtgctgac ctccaaaaga aaccagcttc acgacgaagt ccaccaatgg cgtcgcaacg   7560
```

-continued

```
gagtaggact ggagtttaac cacttgtttg gttacggtgt gcttgatgca ggtgcaatgg   7620
ttaagatggc taaggactgg aaaacagtcc cagagcgctt ccactgcgta ggtggttctg   7680
tccaagaccc tgaaaagatt ccctccactg gcaaacttgt tttgactctt actacagacg   7740
cgtgcgaggg aaaggaaaat ttcgtccgtt acttggagca cgtccaagcc gttatcaccg   7800
taaatgccac cagacgcgga gacttgaaca ttaatatgac ttccccaatg ggcacaaagt   7860
ctatccttct gtccagacgt ccaagagacg atgattcgaa ggttggcttc gataagtggc   7920
ccttcatgac tactcacacc tggggcgaag atgcaagagg cacatggacc ctcgagctgg   7980
gatttgttgg atctgctccc cagaagggag tgctcaagga atggacactg atgctccacg   8040
gcacacagtc ggcccccttac atagaccagg ttgttagaga ttaccaatct aagctcgcta   8100
tgtctaaaaa ggaggagctc gaagaagagc tcgacgaggc cgtagagcgt tccttgaaat   8160
ctatcttgaa caaaaacgga tccggtgcaa ccaactttag cttgctcaag caagccggtg   8220
acgtggagga gaacccaggt ccaatgaaaa aaccagagct tactgcgacc tctgtcgaga   8280
agtttctcat agagaagttc gatagcgtct ctgatctcat gcaattgtct gaaggtgaag   8340
aaagcagagc attttccttc gacgtgggag gaagggggtta cgtgttgcgt gttaactcct   8400
gcgccgatgg attctacaaa gatagatacg tatacagaca cttcgcgtct gcagctctcc   8460
ctatccccga ggtgctcgac atcggtgaat ttagcgagtc tttgacctac tgtatctcca   8520
gacgtgcgca aggagttaca ttgcaagacc ttcccgagac agaactcccc gcggtattgc   8580
agcctgtcgc tgaggctatg gacgccatcg cagcggcgga tctctcccaa acatctggat   8640
tcggtccttt cggtccacaa ggtattggac aatacactac ctggcgcgat tttatttgcg   8700
ctatcgccga cccccacgtt taccactggc aaaccgtcat ggacgacaca gtctccgcat   8760
ctgtcgccca ggcccttgac gaacttatgt tgtgggccga ggattgcccc gaagttcgcc   8820
acttggtgca cgccgacttt ggtagcaaca acgtttttgac tgataacggt cgcatcactg   8880
ccgtcatcga ttggtctgaa gcaatgttcg gagatagcca atacgaagtt gccaacattt   8940
tcttttggag gccatggctt gcctgcatgg aacaacaaac tcgctacttc gagcgcagac   9000
acccagaact cgcaggttcc ccacgtcttc gcgcttacat gttgcgcatc ggattggatc   9060
agttgtacca aagccttgtc gacggaaact tcgacgatgc cgcctgggca caaggacgct   9120
gcgatgcaat cgtgcgctct ggagctggaa ccgtgggaag gacccaaatt gcccgtcgct   9180
ccgcagcagt ctggacagac ggatgcgtgg aagtgctcgc agattctgga aacaggcgtc   9240
cttctacacg cccaagggct aaagaaggat ccggagccac caacttcagc ttgcttaaac   9300
aggcaggaga cgtggaggag aaccctggac caatgaagtt ccagcacact ttcatcgccc   9360
tcttgtctct tttgacctac gcaaacgcac aagaacctgg agcccagcc gctggaatgc    9420 gcaggcgccg ccgcctccaa caagaagatg gaatctcttt cgagtaccac cgctacccag   9480
agttgcgtga agcacttgtg tctgtttggc tccaatgtac cgctatcagc cgtatttaca   9540
ccgttggacg ttccttcgaa ggacgcgaac ttctcgtgat cgagttgtct gacaaccctg   9600
gagtgcacga gcctggagaa cccgaattca gtacatcgg aaacatgcac ggaaacgagg   9660
ctgttggacg tgagcttctc atcttccttg cacaatacct ctgtaacgag taccaaaagg   9720
gaaacgagac catcgtgaac ctcatccaca gcacccgcat ccacatcatg ccttctttga   9780
acccagacgg attcgagaag gccgccagcc aaccaggaga gttgaaagat tggttcgtgg   9840
gacgcagcaa cgcccaagga atcgacttga accgtaactt ccccgacttg gatcgcattg   9900
tttacgttaa cgagaaggag ggaggaccaa acaaccacct cttgaagaac atgaagaaaa   9960
```

-continued

```
ttgtggatca aaacacaaag ttggctcccg agaccaaagc tgttatccac tggataatgg   10020
acatcccatt cgtgttgagc gcaaacctcc acggaggaga cctcgtggca aactacccct   10080
acgacgagac tcgctccgga tccgctcacg agtactcctc ctcccccgat gacgctatct   10140
tccaatccct cgcacgcgca tacagcagct tcaaccccgc tatgtccgac ccaaaccgcc   10200
ccccctgccg caagaacgat gatgactcct ccttcgtgga cggaactaca aacggaggag   10260
cttggtactc cgtgcccgga ggaatgcaag acttcaacta cctcagcagc aactgcttcg   10320
agattaccgt ggagctctcc tgtgagaagt tcccccccga ggagaccctc aaaacctact   10380
gggaggacaa caagaactcc ctcatttcct acctcgagca aattcaccgc ggagtgaagg   10440
gattcgtgcg cgatctccaa ggaaacccca ttgctaacgc taccatctcc gtggagggaa   10500
tcgatcacga tgtgacctcc gctaaagacg gagattactg gcgcctcctc atccccggaa   10560
actacaagct caccgcttcc gctcccggat acctcgctat taccaagaaa gtggctgtgc   10620
cctactcccc cgctgctgga gtggatttcg agctcgagtc cttctccgag cgcaaagagg   10680
aggagaagga ggagctcatg gagtggtgga agatgatgtc cgagaccctc aacttctaat   10740
ctaga                                                                10745
```